United States Patent [19]

Palm et al.

[11] Patent Number: 5,173,796

[45] Date of Patent: Dec. 22, 1992

[54] THREE DIMENSIONAL SCANNING SYSTEM

[76] Inventors: Steven G. Palm, 2119 Pillsbury Ave. S., Minneapolis, Minn. 55404; Elwin M. Beaty, 13529 Arthur St., Minnetonka, Minn. 55343

[21] Appl. No.: 703,285

[22] Filed: May 20, 1991

[51] Int. Cl.$^5$ .............................. G02B 26/08
[52] U.S. Cl. ............................. 359/202; 359/210; 358/208; 250/234
[58] Field of Search ............... 359/201–203, 359/212–214, 220–221, 694, 698, 210, 428; 250/234–236; 356/379–380; 318/632; 358/208, 474, 205

[56] References Cited

U.S. PATENT DOCUMENTS

| | | | |
|---|---|---|---|
| 4,213,146 | 7/1980 | Maiman | 358/208 |
| 4,714,830 | 12/1987 | Usui | 359/202 |
| 5,032,924 | 7/1991 | Brown et al. | 358/208 |
| 5,048,904 | 9/1991 | Montagu | 359/202 |

Primary Examiner—Bruce Y. Arnold
Assistant Examiner—James Phan
Attorney, Agent, or Firm—Leone & Moffa

[57] ABSTRACT

A part scanning and part calibration apparatus and mechanism for the inspection of printed circuit boards and integrated circuits include a camera and two rotating mirrors to scan an image of a pattern mask retical upon which a precise pattern has been deposited. Small parts are placed upon the retical to be inspected. The third overhead mirror is provided to view the part under inspection from another perspective. The scene of the part is triangulated and the dimensions of the system can thus be calibrated. A precise retical mask is provided with dot patterns which provide an additional set of information needed for calibration. By scanning more then one dot pattern the missing state values can be resolved using an iterative trigonomic solution.

5 Claims, 9 Drawing Sheets

PATTERN OF CENTER DOT

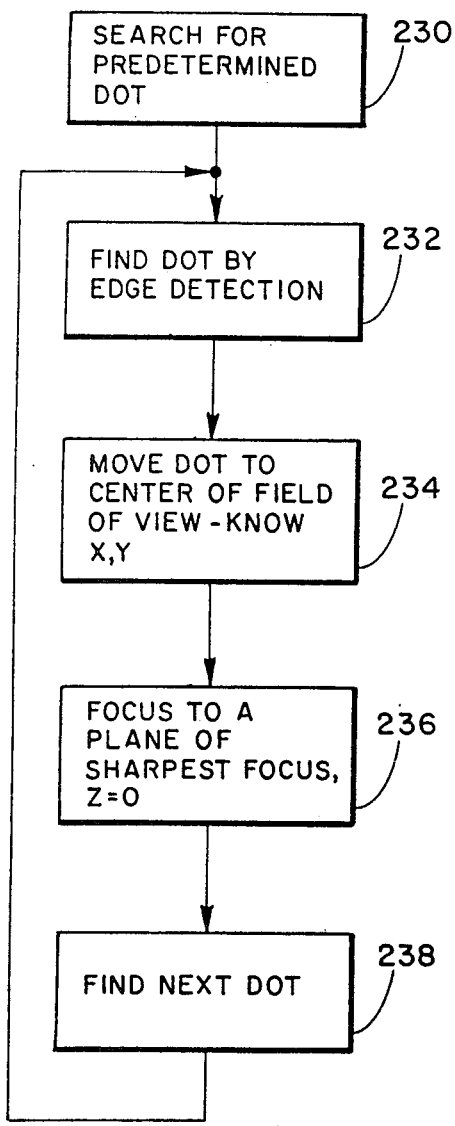
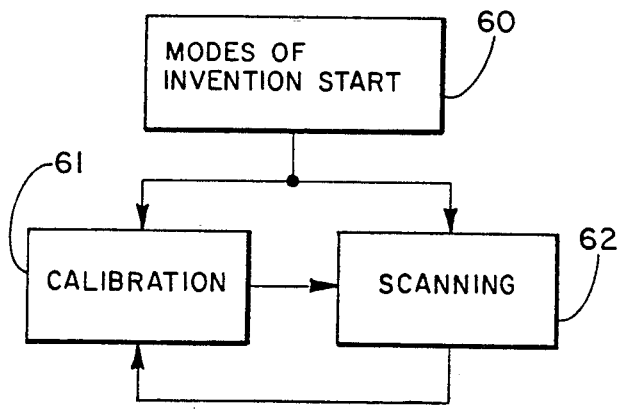

THREE DIMENSIONAL SCANNING SYSTEM

This invention relates to a three dimensional ("3-D") scanner and, more particularly, to a line scanning calibration apparatus involving a single camera with two rotatable mirrors and a third overhead mirror.

BACKGROUND OF THE INVENTION

Prior art 3-D line scanners have involved multiple access mirrors and multiple cameras. Scanners have been used to inspect printed circuited boards integrated circuits and other small parts. The prior art requires two cameras and a multiple number of mirrors to accomplish the scanning mechanism. Traditional prior art scanning algorithms utilize a triangulation method that requires two mirrors. Multiple cameras increase the cost of prior art solutions as well as the complexity.

Prior art part scanning apparatus have utilized a "golden part" for calibration of the scanning operation. A golden part is a part that is precisely dimensioned in a coordinate system, as for example, a Cartesian coordinate system using x, y, and z coordinates. The golden part provides an extremely precise image of the parts that are to be inspected with the scanner. The golden part typically is extremely expensive to produce and in some cases very difficult to produce. A unique golden part must be produced for each unique part design. The difficulty and expense arises from the need to provide a golden part that has extremely high tolerances, sometimes less than 10 millionths of an inch. Such precision is required for each different golden part created.

The golden part is scanned by the scanner of the prior art and is used to create a "trained image". The trained image is then used to match up a image of an inspected part to calibrate the scanner of the prior art. The prior art method requires a golden part to have at least 10 times more accuracy than the part to be inspected. It is therefore one motive of the invention to eliminate the need for the construction of a "golden" part for each and every part to be inspected by the part scanning apparatus.

SUMMARY OF THE INVENTION

The invention provides a method of inspecting a three dimensional part using a single axial camera that receives an optical input through a set of two mirrors. A third mirror is provided to provide a top view of the part. The mirrors are precisely rotatable such that the operator is aware of the exact location of the mirror. The mirrors are calibrated with a method of the invention using a novel triangulation technique. The calibration method proceeds by first noting the position of the two rotatable mirrors and the position of the camera. A precise auto-focus mechanism is incorporated that allows the feedback of focus vs. distance information to the controller of the system. During calibration a precisely defined object such as a reticle mask is employed to provide a set of dimensional data that is invariate over the system parameters. The reticle mask has a precise pattern whose featured dimensions are precisely known. The calibration method proceeds by creating a set of state equations that completely describe the ray of light traversing from the camera through the first and second mirrors and onto the reticle. The ray of light is assumed to be focused from the auto-focusing mechanism at a predetermined relative distance. The calibration method of the invention proceeds by then introducing a third overhead mirror that provides a second set of state equations. The first and second set of state equations can then be solved using an iterative method whereby unknown values of the states can be determined by algebraic manipulation.

It is one object of the invention to provide an improved method of part inspection that utilizes a single camera to analyze the part in three dimensions.

It is yet another object of the invention to provide an improved line scanner that can inspect parts in three dimensions using a precisely defined reticle mask.

It is yet a further object of the invention to provide an improved part scanning mechanism that is lower in cost.

It is yet a further object of the invention to provide an improved scanning mechanism that allows the three dimensional characterization of a part.

It is yet a further object of the invention to provide an improved part scanning calibration system that can be auto-focused and does not need manual intervention.

It is yet a further object of the invention to provide an improved part scanning mechanism which provides for a single camera with two precisely located mirrors and which correlates the rotational angle of each mirror to the displacement in a focused image of a mask reticle.

It is yet a further object of the invention to provide an improved line scanning mechanism whereby the second triangulation camera is eliminated.

It is yet another object of the invention to provide a part scanning calibration mechanism that does not require use of a golden part.

It is yet another object of the invention to provide a reticle mask that has small pattern features that have been photo-deposited on a plate with high accuracy.

It is yet a further object of the invention to use a lower cost lower resolution camera as the optical detector of the system.

It is still a further object of the invention to provide an improved dot scanning system whereby the edge of a dot is found using an edge detection algorithm.

It is yet a further object of the invention to use an auto-focusing camera to determine the path length of a ray of light reversing from an object to be scanned in the camera.

BRIEF DESCRIPTION OF THE DRAWINGS

FIG. 9 is a schematic flow diagram method of one example of the characterizing the plane for all dots on the reticle.

FIG. 10 is a mode diagram of the operation of the invention.

DETAILED DESCRIPTION OF THE PREFERRED EMBODIMENT

Figure 1:
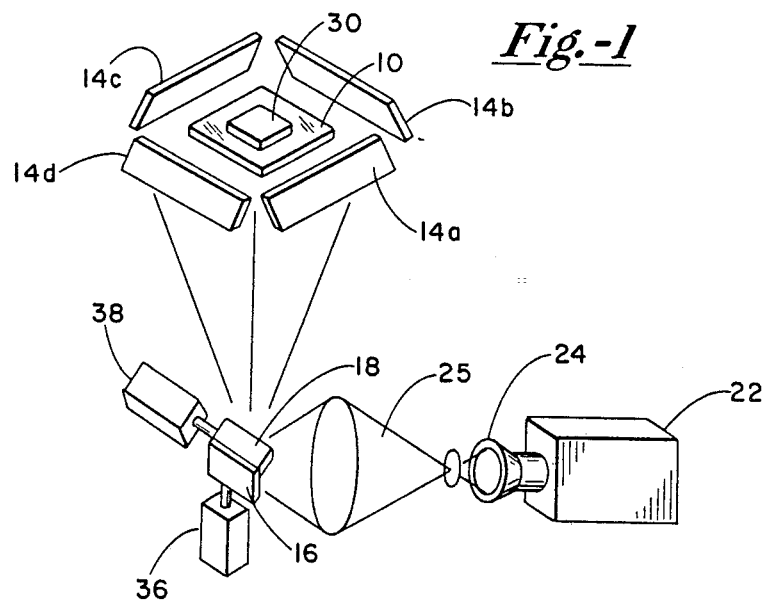
FIG. 1 is a schematic diagram of the apparatus of the invention.

FIG. 1 shows the method and apparatus of the three dimensional scanning system of the invention. FIG. 1 shows a CCD camera 22 with an auto-focusing zoom lens 24. The auto-focusing zoom lens 24 is trained on an optical system 25 that views a set of mirrors. The set of mirrors are composed of a Y axis mirror 16 and an X axis mirror 18 gazing on a set of 4 overhead mirrors 14A, 14B, 14C and 14D as well as a reticle 10 having a generally planar shape. The Y mirror 16 is controlled by a Y servo-motor 36. The X mirror 18 is controlled by an X servo-motor 38. The reticle 10 is used as an optically transmissive support for a part 30 to be scanned. The mirror's optical system 25 and auto-focusing zoom 24 provide an image of the part as well as an image of the reticle 10. The mirror system described above provides an apparatus that can view the part from above and below a plane defined by the reticle 10.

Figure 2:
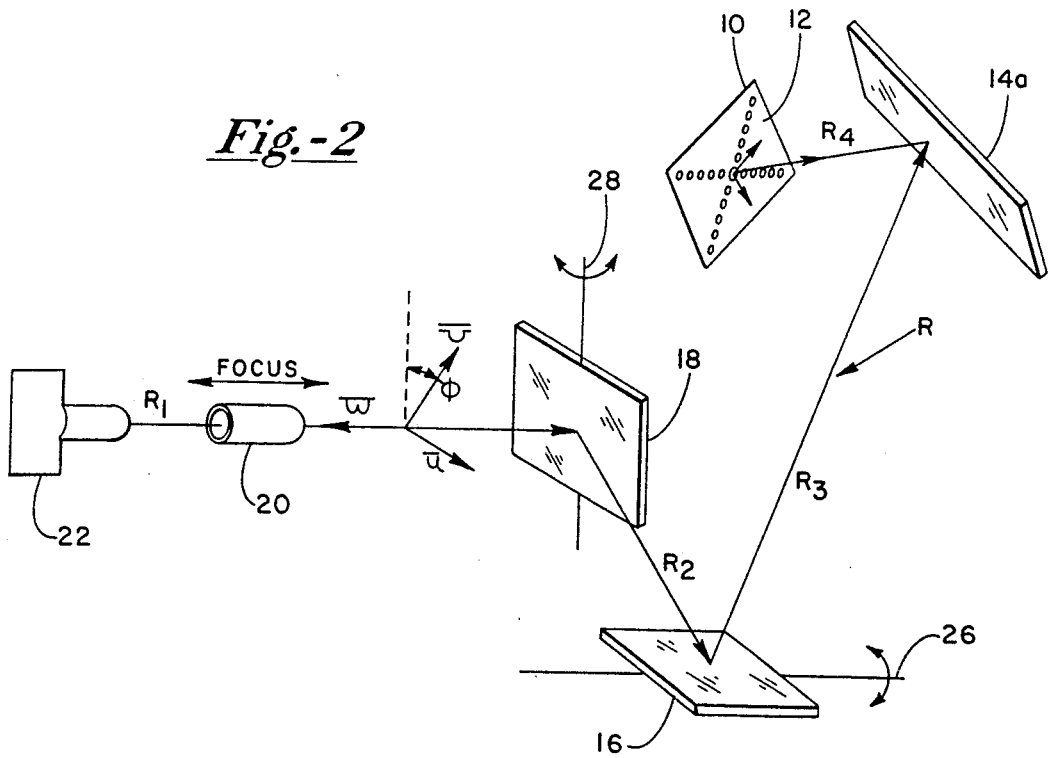
FIG. 2 is a three dimensional perspective representation of the retracing method of the invention.

FIG. 2 shows a three dimensional perspective schematic representation of one embodiment of the apparatus of the invention used to scan and calibrate an optical scanning system. The apparatus of the invention includes a camera 22 which receives an image through an auto-focusing zoom lens 20. The auto-focusing zoom lens 20 provides a means to focus a set of incoming optical rays R into the cameras lens 22. The auto-focusing mechanism provides a relative means of determining the path length of an optical ray in that there is a relationship between the distance where an object will become focused and the amount of focusing adjustment done by the optical automatic auto-focusing system. In the method of the invention the reticle 10 has deposited upon it a pattern 12. The pattern 12 provides a number of features for the invention. The reticle pattern 12 provides a means to accurately access the size and relative position of images in the optical system. The analysis of the method of the invention proceeds by analyzing the tracing of an optical ray from the target to the imaging device. In the diagram of FIG. 2 the ray is proceeding from the reticle pattern to the overhead mirror 14A to the Y mirror 16 then to the X mirror 18, then through the auto-focusing system, then to the camera. Each ray R4, R3, R2 and R1 has associated with it three dimensional coordinates XYZ.

When the apparatus of the invention is first turned on it requires calibration. In the method of calibration provided by the instant invention, the positions of the X and Y mirrors are known precisely as well as the position of the camera 22. The calibration mechanism takes advantage of the fact that the pattern on the reticle provides a precise image in the CCD camera 22. The angular displacements of the X and Y mirror shown around the Y mirror axis 26 and the X mirror axis 28 are not known before calibration. Also, the location of the overhead mirror 14A and its angular inclination with respect to the optical ray R3 is not known. The method of the invention proceeds by characterizing the optical ray R traversing through the mirrors and optical systems and creating a set of system equations that can be solved for unknown variables. The precisely created reticle 12 provides the information needed to solve the system of equations for the precise location of the overhead mirror 14A and the optical axis 26 of the Y mirror and the optical axis 28 of the X mirror. In the calibration of the invention the reticle is viewed in two different sets, first is viewed from the bottom using the rotatable mirrors. And secondly, it is viewed from the top using the overhead mirror. The two views are necessary to scan the parts 30 in 3 dimensions. The bottom view provides a precise profile view of the object. The bottom view or the plane of the reticle 10 is defined in the optical system as the Z=0 position.

Figure 3:
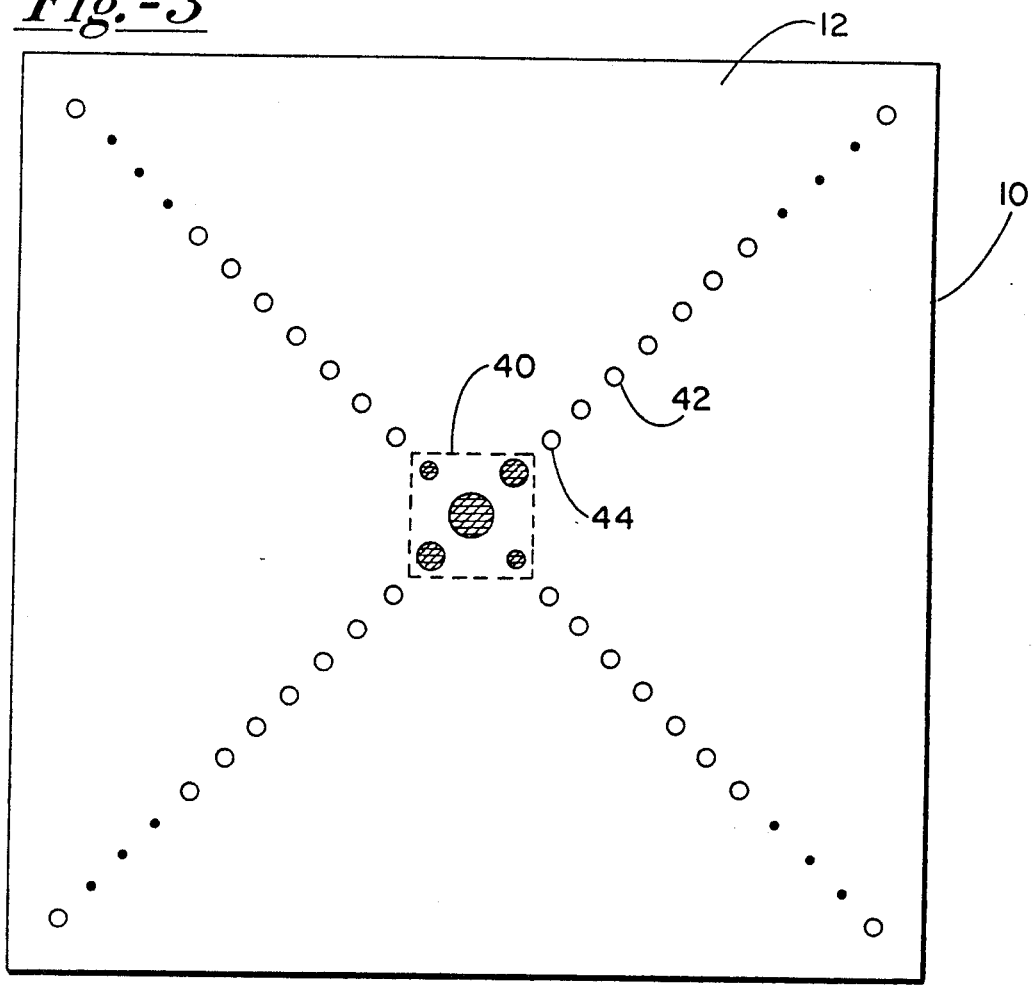
FIG. 3 is a representation of the mask reticle pattern as employed in one embodiment of the invention.

Now referring to FIG. 3, the precise reticle pattern 12 is shown. The precise reticle pattern 12 is drawn or advantageously photo-deposited on reticle 10. The pattern shows a precise geometry that can be used to accurately calibrate the optical system of the method of the invention. The reticle pattern is a diagonal set of circles or dots, for example, that are precisely spaced and have a precise size. All features on the reticle have a known shape and a known size. The size and shapes and locations are predetermined prior to the calibration of the invention. Other sizes and shapes may be employed to accomplish the function of the reticle 10 and the description herein is meant by way of example and not limitation. The center of the pattern comprises a pattern of 5 dots 40 within the broken line used for the initial calibration of the apparatus of the invention. A second dot 44 is used to determine the orientation of the reticle space relative to the center dot pattern 40. Other dots shown here as 42 are used to characterize the reticle plane. The position of the dots are defined as Z=0 everywhere on the reticle 10, that is, the reticle is assumed to be a plane in three dimensional space and the plane that the reticle exists in is defined as the Z=0 plane.

Figure 4:
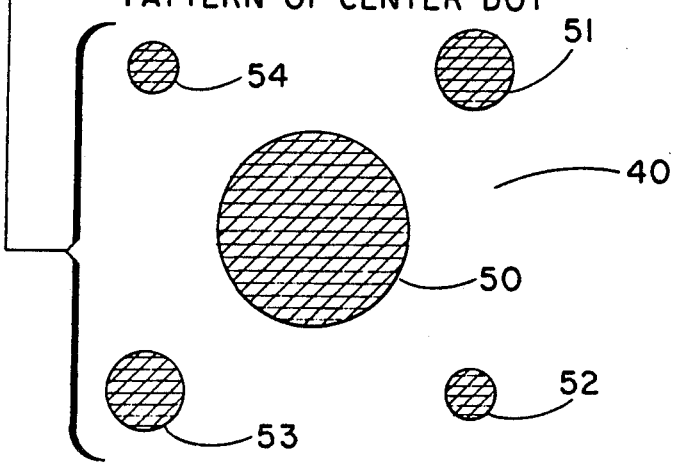
FIG. 4 is a representation of the dot pattern of the center dot of the precision reticle mask as employed in one embodiment of the invention.

Now referring to FIG. 4 which shows a detail enlargement of the center dot pattern 40 of FIG. 3. The center grouping of dots 40 shows a large central dot 50 surrounded by four peripheral dots 51, 52, 53 and 54. The large center dot 50 is used by the focusing and positioning system of the invention to accurately locate and position the center of the reticle. This dot is predetermined to be at the center of the reticle 10. The peripheral dots 52 and 54 are used as diagonal positioning dots as well as the dots 53 and 51. The size of the dots are varied to indicate rotational position of the reticle in that dot 53 is different in size from dot 52. Dot 54, 52 and 51 are different sizes but are advantageously smaller than dot 53. Those skilled in the art will understand that this mask pattern is provided as one method of fixing a three dimensional precise shape in that other patterns can be used to provide a precise shape such as cross hatching or linear lines with cross tick marks.

Referring now to FIG. 5B, a high level flow diagram of the calibration method of the invention is shown. The process of calibrating the invention first starts at block 100 by fixing the center of the center dot pattern 40 shown. The process then flows to block 102 wherein the optical system looks at the center dot pattern and obtains an absolute center from the pattern 40. The process then flows to block 104 where the display and camera are calibrated to calculate a scale factor for the X and Y directions. The process then flows through schematic block 106 where the aspect ratio of the camera is determined as the dimension X divided by the dimension Y. The process then flows to 108 where the other dots are determined. The other dots are found and their sizes determined which orients the reticle pattern and is used to calculate the characterization of the rest of the optical system. The process then flows to block 110 wherein the rest of the reticle pattern is characterized and the optical system is calibrated. Each block will in turn be detailed with reference to the following FIGS. 6, 7, 8 and 9.

Now referring to FIG. 5A showing the method of calibrating the invention's top mirror shown in FIG. 1 as mirror's 14A, 14B, 14C and 14D. The method of the calibrating the top mirrors is similar to the method of calibrating the reticle pattern and the method of calibrating the axis of the X mirror 28 and Y mirror 16 as shown in FIG. 2. Similar to the reticle, an axis alignment of process shown is FIG. 5B, the process in FIG. 5A starts by fixing the center of a image on the CCD and processing the rays from the image into the CCD camera. The method of looking at the center dot is described in FIG. 7. The advantage at this point in the calibration method of the invention is that the axial mirror displacements have now been calibrated, the axial mirror axis' shown on FIG. 2 as 28 for the X mirror and 26 for the Y mirror. This enables the apparatus and method of the invention to calibrate a third unknown optical surface which is the overhead mirror 14A shown in FIG. 2. The process of FIG. 5A then flows to looking at the center of the dot pattern 102A. The optical axis and the focal optical path lengths from the image can be correlated using the methods of FIG. 16. The process then flows to block 102A where the dot pattern absolute center is determined by edge detection. Those skilled in the art will recognize that certain methods of edge detection such as subpixel edge detection could be used to more accurately find the position of the dots. Those skilled in the art will understand that alternative methods of edge detection could also be used. The process then flows to block 104A where the position of the overhead mirrors are determined by using the optical path of the mirror and solving for the state variables of the ray tracing equation. Ray tracing and vector analysis is well known in the art. A good description of vector analysis can be found in a book entitled *Introduction to Vector Analysis* by Harvey F. Davis and Arthur David Snyder, 4th Edition, published by Allyn and Bacon, Inc. A good review of retracing can be found in a December 1990 Byte article entitled *Retracing for Realism*, in which the mechanism of retracing is described. Both articles are hereby incorporated by reference. The process then flows to 106A where the aspect ratio's are calculated again. The process then flows to 108A in which the other dots in the reticle pattern are scanned and the overhead mirrors are further characterized. The process then flows to 110A where the plane of the reticle is characterized.

Figure 5:
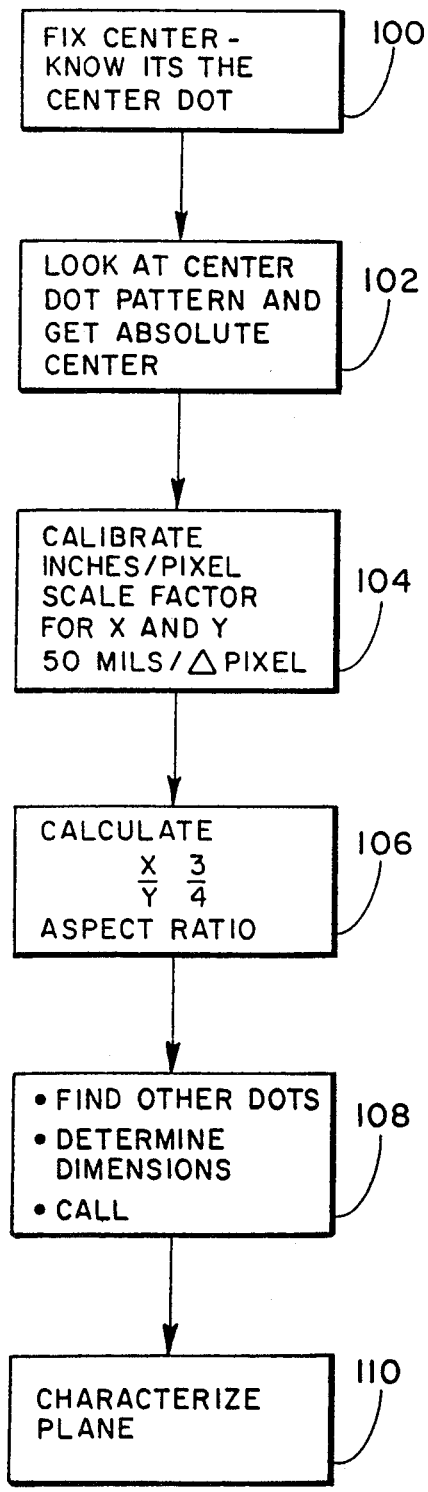
FIGS. 5a and 5b are flow diagrams showing a method of calibrating of the invention.
Figure 6:
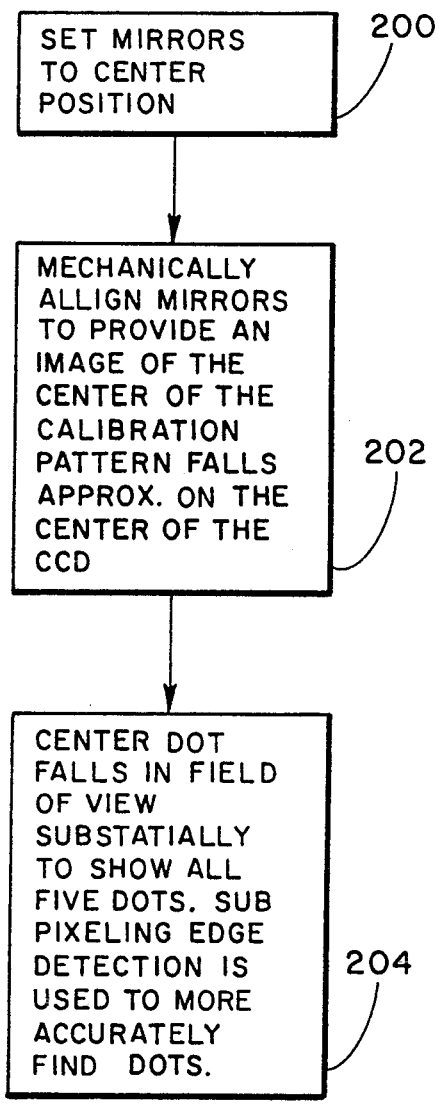
FIG. 6 is a flow diagram showing a method of fixing the center of a dot as employed by the invention.

FIG. 6 shows a flow diagram for fixing the center dot pattern 40 which is shown as block 100 in FIG. 5. The system first sets the mirrors 16, 18 to their center positions in block 200. All apparatus references refer to FIGS. 1 and 2. The X mirror 18 and the Y mirror 16 are positioned such that if they rotated either way an equal amount, their deflections would be roughly in the center. The process of fixing the center then flows to block 202 where the mirrors 16, 18 are mechanically aligned to provide an image of the center of the calibration pattern so that it falls directly on the center of the CCD array in CCD camera 22. The alignment of the mirrors allow the mechanisms that move the mirrors 16, 18 to adequately provide a range of motion that scans both the CCD camera 22 and the object or part 30 on the reticle. The process of fixing the mirrors then flows to 204 where the center dot falls on the field of view of the CCD camera to substantially show all five dots in the center dot pattern 40. The process then flows to 102 in FIG. 5 to look at the center dot pattern.

Figure 7:
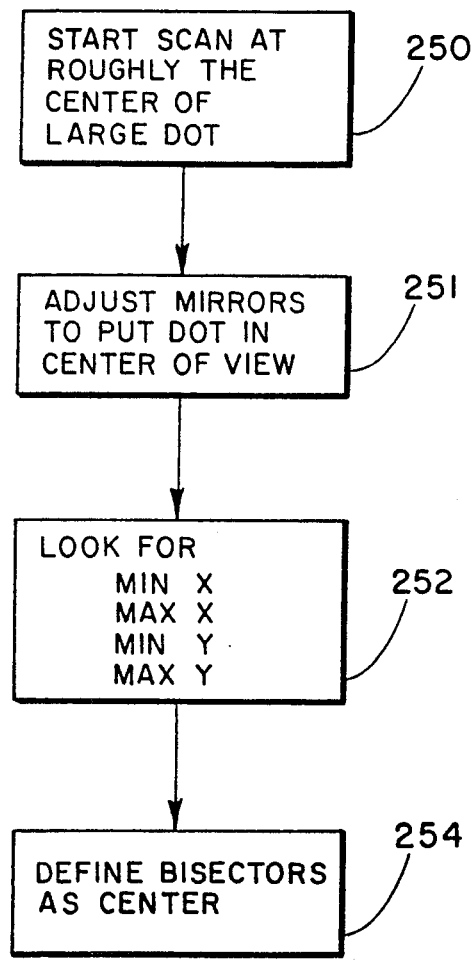
FIG. 7 is a schematic flow diagram of the method of looking at a center of a dot as employed in one embodiment of the invention.

Referring now to FIG. 7, the method of determining the position of the center dot 50 is shown. The process starts at block 250 where the scan of the pattern is roughly at the center of the large dot. The process then uses conventional edge detection techniques that look for a minimum X and a minimum Y and maximum X and maximum Y for the dot. The mirrors are adjusted in process block 251 to locate the dot in the center view of the CCD camera 22. After the minimum X, minimum Y and maximum X and maximum Y are determined from edge detection methods known in the prior art, the bisectors of the centers are found and the precise center of the dot is determined in process block 254.

Referring back to FIG. 5, the scale factors of the invention of the apparatus are determined by dividing the number of mils by the number of pixels. This is determined by knowing that the center dot pattern 40 is a certain size, for example, in this case 50 mils and the number of pixels that cross the center are known. In this case, for example, 100 pixels indicates that the mils per pixel to be 50/100 or the aspect ratio would be ½. The same procedure can be used to determine the scale factor for Y. The process then flows to calculate the aspect ratio 106 of Y to X. The process then flows to 108 where the other dots are scanned and the dimension of the precise reticle pattern are used to calibrate the optical system.

Figure 8:
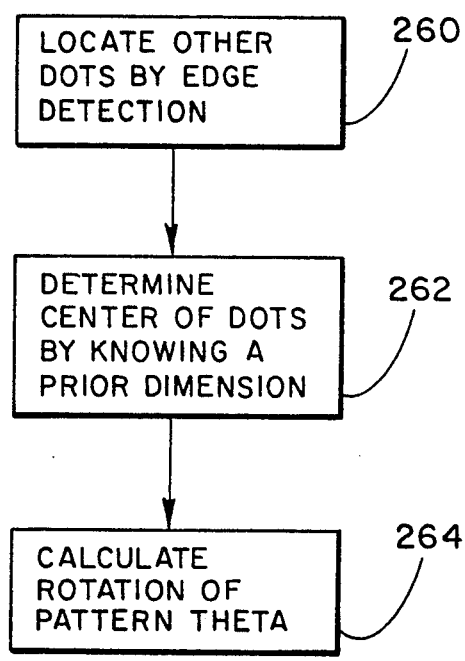
FIG. 8 is a schematic flow diagram of the method of calculating the angle of a mirror.

FIG. 8 shows the method of calculating the angular displacement of the mirrors knowing the size and relative aspect ratios of the pixels in the invention. In block 260 another dot is found by edge detection. The edge detection method of the invention is outlined in FIG. 7. The additional dot's position is in a predetermined known location. This provides a method of determining a system of equations for the first dot and the second dot. The absolute position of the two dots are known which provides sufficient information to determine the angular displacement verses linear displacement of the object on the CCD screen.

Referring now to FIG. 2 which shows the Y mirror 16 and the X mirror 18 undergoing a reflection of a ray R, compared of R1, R2, R3 for every displacement of mirror X and mirror Y the image associated will move in a certain direction. By watching the motion of the relative dot on the screen, the location and calibration of mirrors can be accomplished. For every angular displacement of the Y mirror there will be an associated Y linear displacement of the image. For every angular displacement of the X mirror there will be an associated displacement of the X image.

Referring now to FIG. 9 where the characterization of the Z=0 plane is accomplished. In step 230 the remainder of the dots are checked and searched for. Each dot is found by edge detection as shown in FIG. 6 process step 232. The process then moves to step 234 where each dot is positioned to the center of the field of view and the location of the dot is memorized. The process then flows to step 236 where the plane of sharp is focused Z=0 is determined. The length of the optical path can now be related to the distance that the Z plane is determined to be by defining the Z plane to be 0 at this location. The process then flows to block 230 where the next dot is found and the same process is repeated back to step 232.

Referring now to FIG. 10, two modes of the operation of the invention are shown. The invention is shown starting in the start mode 60 and either can go immediately into the scanning mode 62 or the calibration mode 61. If the invention is in calibration mode 61 it can at any time go into the scanning mode 62. The invention, while in scanning mode can any time go into the calibration mode 61. Thus, the invention provides a method of automatically calibrating and scanning dynamically during the operation of a scanning operation. During the operation of a scanning mode. The invention thus provides a way of compensating for temperature variations in the optical characteristics of the materials as well as in a vibrational related changes or simply changes due to moving the part or moving the apparatus.

Now referring to Table A which shows a listing of the model for the method of the invention. The invention utilizes a model structure of the apparatus of the invention that forms a computing structure. The models is given below as a list of data types with data representations and line numbers. The first model is the model of the optical system of the method of the invention. The elements of the model consist of a type which tells what kind of model type it is. In line 422 a unit-type which tells what kind of unit-type it is. In line 423 a model label which labels the model in 424 is given. In line 425 a calibration time for the model which is given. In line 426 a number of surfaces in the model which is given. The surface structure is described below in line 427. The number of different paths that there exist in the model are described in line 428. The optical path structure is given in line 430. The next line is a two dimensional array that defines a viewpoint at the optical origin. The next model element is the camera roll angle at line 434 which describes the angle between the original view and the X axis in world coordinates. The next element of the model is on line 437 which is the focusing model which is described below. The final element of the model is the mirror model which is a mirror model structure described below.

TABLE A

| 419 | /* Model structure */ | |
|---|---|---|
| 420 | struct MODEL | |
| 421 | { | |
| 422 | BYTE Type; | /* model type */ |
| 423 | BYTE UnitType; | /* unit type */ |
| 424 | char Label[LABELSIZE]; | /* model label */ |
| 425 | time_t CalibTime; | /* last time & date the system was calibrated */ |
| 426 | BYTE NumberOfSurfaces; | /* number of different surfaces in model */ |
| 427 | struct SURFACE[MAXSURFACES];/* array of surfaces */ | |
| 428 | BYTE NumberOfPathes; | /* number of different pathes in model */ |
| 429 | /* array of optical pathes */ | |
| 430 | struct OpticalPath[MAXOPTICALPATHES]; | |
| 431 | /* the unit vectors u,v,w that define the view plane at the optical origin */ | |

TABLE A-continued

| 432 | double OriginViewUnit[VECT3] [VECT3]; | |
|---|---|---|
| 433 | /* angle between OriginViewVector u and x axis world vector(1,0,0) */ | |
| 434 | float CameraRollAngle; | |
| 435 | /* the ratio of ViewDim[U]/ViewDim[V]; assumed constant for all views */ | |
| 436 | double AspectRatio; | |
| 437 | struct FOCUSMODEL FocusModel; /* structure describing focus */ | |
| 438 | struct MIRRORMODEL MirrorModel[VECT2]; /* x & y moving mirror models */ | |
| 439 | }; /* end od struct MODEL */ | |

Now Table B refers to a structure for the surface of a optical element in the system. Table B lists a surface type whether it is reflective or refractive in line 388. The surface has a label on line 389, the refractive index of the surface is given on 390, the position in the world of the surface is given in line 391. The normal vector is given on line 393 which is the unit world vector normal to the surface anchored at the position vector given on line 391.

TABLE B

| 385 | /* Optical Surface structure */ | |
|---|---|---|
| 386 | struct SURFACE | |
| 387 | { | |
| 388 | BYTE Type; | /* surface type: REFLECT. REFRACT */ |
| 389 | char Label[LABELSIZE]; | /* surface label */ |
| 390 | float RefractiveIndex; | /* refractive index, past the surface */ |
| 391 | double Position[VECT3]; | /* world surface position */ |
| 392 | /* unit world vector normal to the surface anchored at the position vector */ | |
| 393 | double Normal[VECT3]; | |
| 394 | }; /* end of struct SURFACE */ | |

Table C refers to the optical path structure which details an optical path in an ordered list of surfaces. The optical path contains a type on line 407, a label on line 408, a lightswitch byte on line 409 and another surface byte on line 410, a surface index structure byte on line 411, and a surface structure on line 413 which has been previously described.

TABLE C

| 402 | /* Optical Path Structure */ | |
|---|---|---|
| 403 | /* an optical path is a ordered list of surfaces */ | |
| 404 | /* optical path types are the same as scan types */ | |
| 405 | struct OPTICALPATH | |
| 406 | { | |
| 407 | BYTE Type; | /* optical path type */ |
| 408 | char Label[LABELSIZE]; | /* optical path label */ |
| 409 | BYTE LightSwitches; | /* bite to turn for lights */ |
| 410 | BYTE NumberOfSurfaces; | /* number of surfaces along the path */ |
| 411 | BYTE SurfaceIndex[MAXSURFACES]; /* array of indexes to the surfaces */ | |
| 412 | /* array of pointers to the surfaces in the optical path /* | |
| 413 | struct SURFACE far *SurfacePtr[MAXSURFACES];/* not dynamically allocated */ | |
| 414 | }; /* end of struct OPTICALPATH */ | |

Now referring to Table D which is a focusing model structure. The focus model contains three elements which determine the focus of the ray traced in the method of the invention. The first element is a coefficient V which is a one dimensional vector of polynomial coefficients used to compute V of the view dimension vector from the focus position using the routine that will be described below. The next element is a coefficient of W which is a one dimensional vector which is a vector of polynomial coefficients used to compute W of the view dimension vector from the focus position and the final element is defined on line 358 as a coefficient of the optical path length which is a one dimensional vector of polynomial coefficients used to compute the optical path length from the focus position.

TABLE D

| | |
|---|---|
| 347 | /* Focus Model Structure */ |
| 348 | struct FOCUSMODEL |
| 349 | { |
| 350 | /* polynomial coefficients used to compute V of the ViewDim vector */ |
| 351 | /* from the focus position  */ |
| 352 | float CoeffV[VECT3]; */ |
| 353 | /* polynomial coefficients used to compute W of the ViewDim vector */ |
| 354 | /* from the focus position  */ |
| 355 | float CoeffW[VECT3]; |
| 356 | /* polynomial coefficients used to compute the optical path length(op1) */ |
| 357 | /* from the focus position  */ |
| 358 | float CoeffOPL[VECT3]; |
| 359 | }; /* end of struct FOCUSMODEL */ |

Table E describes a mirror model structure which is simply a one dimensional vector of coefficients that contain the polynomial coefficients to compute the mirror angles from a mirror position.

The foregoing tables describe the optical system of the method of the invention with regard to the elements of the structure of the invention disclosed above and in relation to the full programming model of the invention listed in Appendix A. Line numbers in Tables A, B, C, D and E correspond to line numbers in the C programming language program found in Appendix A.

TABLE E

| | |
|---|---|
| 361 | /* X & Y Mirror Model structure */ |
| 362 | struct MIRRORMODEL |
| 363 | { |
| 364 | /* polynomial coefficients to compute mirror angles from mirror position */ |
| 365 | float Coeff[VECT3]; |
| 366 | }; */ end of struct MIRRORMODEL */ |

Figure 11:
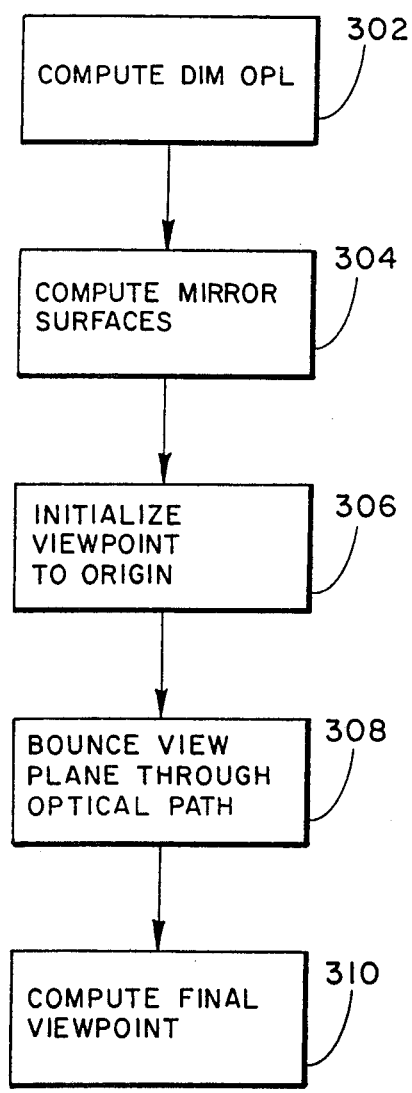
FIG. 11 is a process flow diagram for computing the view plane.

Referring now to FIG. 11, a flow diagram of a method of computing the view plane as contemplated by the present invention is shown. The method comprises the steps of computing dimensions and optical path length ( "OPL" ) 302, computing the location of the X,Y mirror surfaces 304, initializing a view point to origin 306, bouncing the view plane through the optical path 308 and computing the final view point 310. At step 302 the algorithm computes the dimensions and optical path length. Once the optical path length is known the process proceeds to step 304 where the location of the mirror surfaces for mirrors 16 and 18 are determined. Having determined the mirror surface locations, the method proceeds to step 306 wherein the view point is initialized to be the origin at coordinates 0,0,0. Next, at step 308 the view plane is reflected or bounced through the optical path. The final view point can then be computed at step 310.

Figure 12:
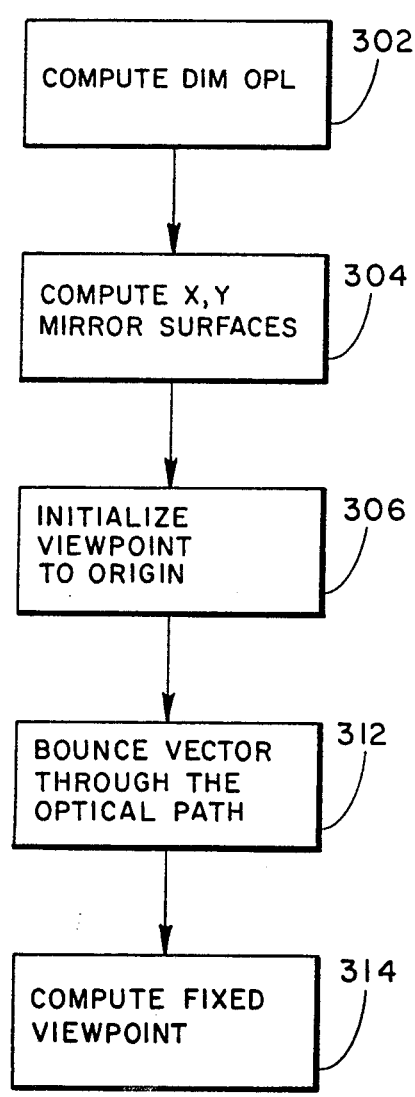
FIG. 12 is a process flow diagram for computing the view point.

Referring now to FIG. 12, a flow diagram of a method of computing the view point as contemplated by the present invention is shown. The method comrises the steps of computing dimensions and optical path length ( "OPL" ) 302, computing the location of the X,Y mirror surfaces 304, initializing view point to origin 306, bouncing a vector through the optical path 312 and computing the final view point 314. At step 302 the algorithm computes the dimensions and optical path length. Once the optical path length is known the process proceeds to step 304 where the location of the mirror surfaces for mirrors 16, 18 are determined. Having determined the mirror surface locations, the method proceeds to step 306 wherein the view point is initialized to be the origin at coordinates 0,0,0. Next, at step 312 a vector is reflected or bounced through the optical path. The final view point can then be computed at step 314.

Figure 13:
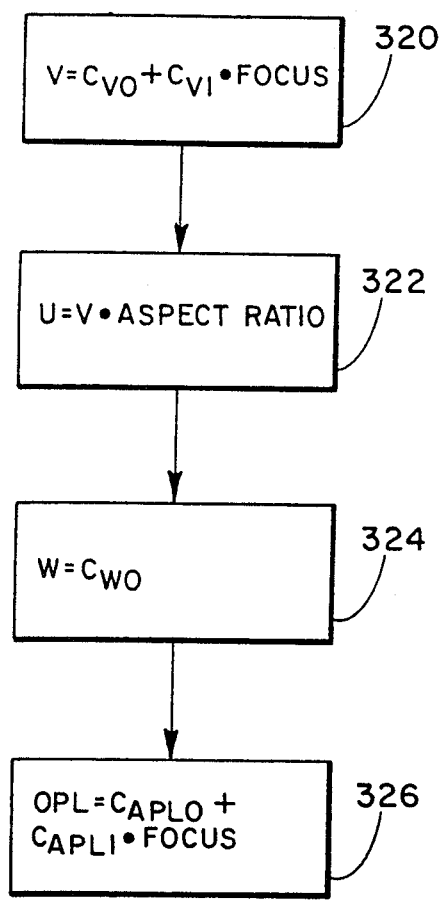
FIG. 13 is a process flow diagram for computing the OPL coefficient.

Referring now to FIG. 13, a flow diagram of a method of computing the dimensions and optical path length as contemplated by the present invention is shown. The method comprises the steps of computing the parameters V at step 320, U at step 322, W at step 324 and OPL at step 326. Starting at step 320 V is found by computing the equation $$V = C_{v0} + C_{v1} * \text{focus}.$$

Then, at step 322 U can be solved according to the equation $$U = V * \text{Aspect ratio}.$$

Next, at step 324 W is solved by the equation $$W = C_{w0}.$$

Finally, the optical path length OPL can be determined by $$OPL = C_{opl0} + C_{opl1} * \text{focus}.$$

Figure 14:
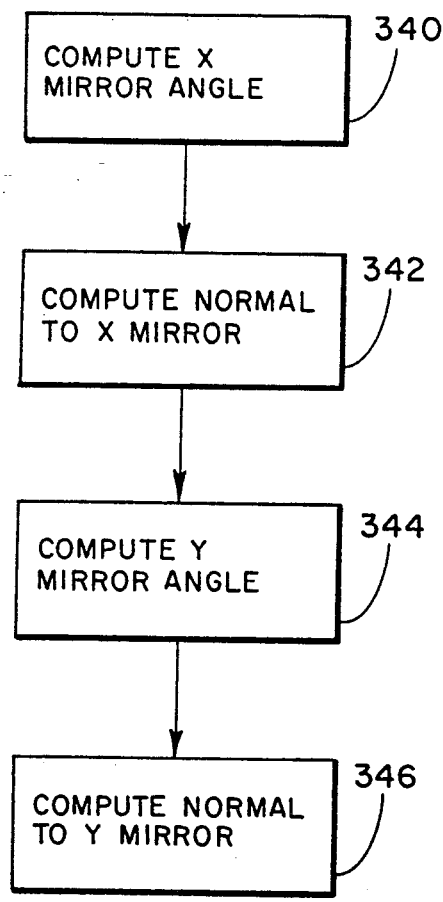
FIG. 14 is a process flow diagram for computing the mirror surfaces.

Referring now to FIG. 14, a flow diagram of a method of computing the location of the mirror surfaces as contemplated by the present invention is shown. The steps for this computation include computing the X mirror angle 340, computing the normal to the X mirror 342, computing the Y mirror angle 344 and computing the normal to the Y mirror surface 346.

Figure 15:
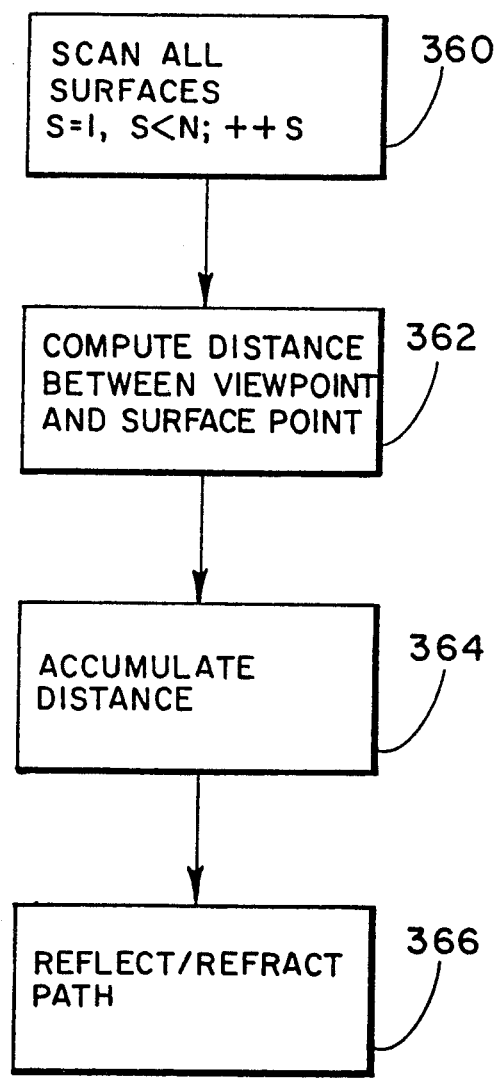
FIG. 15 is a process flow diagram for bouncing the view plane through the optical path.

Referring now to FIG. 15, a flow diagram of a method of bouncing the view plane through the optical path as contemplated by the present invention is shown. The steps comprise scanning all surfaces 360, computing the distance between the view point and surface point, accumulating the distance 364 and reflecting and refracting the path 366.

Figure 16:
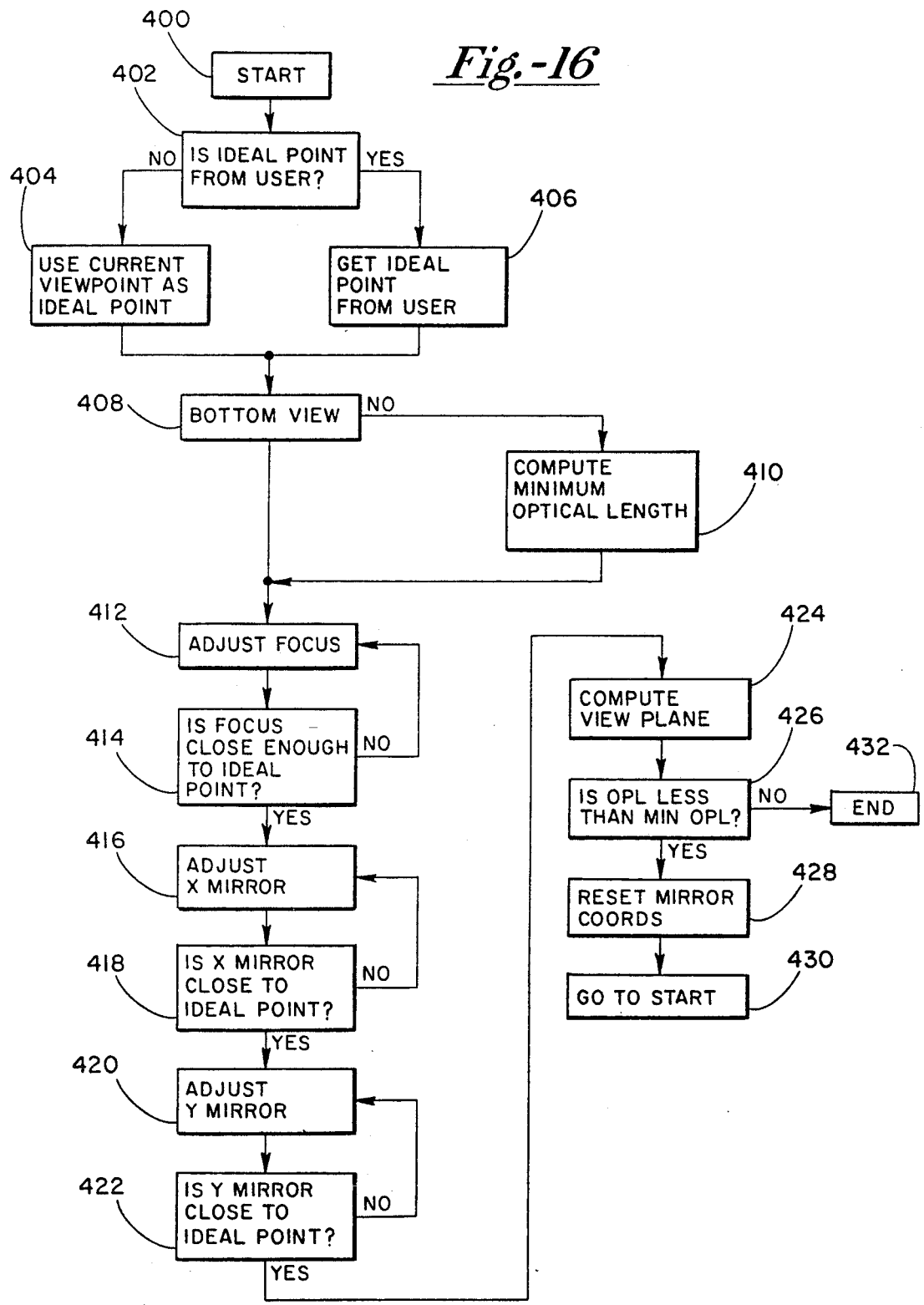
FIG. 16 is a process flow diagram for computing the mirror position.

Now referring to FIG. 16 which shows the method of computing the mirror position from the view point. The method starts at process flow block 400. Process flow block 402 requests whether the ideal point is entered from the user. If it is, the process flows to process flow block 406 to get the ideal point from the user. If the ideal point is not to be gotten from the user in process block 402 the process flows to process block 404 to use the current view point as the ideal point. The process flows in either case to process block 408 to check whether the view is a bottom view. If it is a bottom view the process flows to process block 412 to adjust the focus. If it is not a bottom view the process flows to process block 410 to compute the minimum optical path length. In either case the process flows to process block 412 to adjust the focus. The process then flows to process block 414 to check whether or not the focus is close enough to the ideal point, if it is not the process flows back to process block 412. In process block 412 the focus is adjusted until such time that the focus is close enough to the ideal point. When the focus is close enough to the ideal point the process flows to process block 412 to adjust the X mirror position. The process then flows to process block 418 to check whether the X mirror position is close to the ideal point. If it is not, the process flows to process block 416 to adjust the X mirror position. If in process step 418 the X mirror is close enough to the ideal point the process flows to process block 420 to adjust the Y mirror position. The process then flows to process block 422 to check whether the Y mirror position is close to the ideal point, if it is not the process flows to process block 420 to adjust the Y mirror position. If the Y mirror position is close to the ideal point the process flows to process block 424 to compute the view plane. The process flows to process block 426 to check whether the optical path length is less than the minimum optical path length. If it is not, the process ends at process step 432. If the optical path length is not less than the minimum optical path length then the process flows to process block 428 to reset the mirror coordinates. The process then flows to process block 430 to return to the start.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

Appendix A

```
1   /*******************************************************************
2
3       Module Name: qfp.h
4
5       Software Copyright (C) 1991
6       Scanner Technologies Corp., MPLS, MN. All Rights Reserved.
7
8       Description: This module contains the major structure definitions
9           macros, and global variables, for the cyclops inspection
10          program.
11
12      Notes:
13
14  *******************************************************************/
15  #include <TIME.H>        /* header file for time variables and functions */
16
17  /*******************************************************************/
18  /* Macro Definitions                                                */
19  /*******************************************************************/
20  #define PASS       TRUE
21  #define FAIL       FALSE
22
23  #define LABELSIZE 10     /* label size is limited to 10 characters */
24  #define VECT2      2
25  #define VECT3      3
26  #define ROW3       3
27  #define COL3       3
28
29  #define X          0
30  #define Y          1
31  #define Z          2
32
33  #define U          0
34  #define V          1
35  #define W          2
36
37  /* unit types */
38  #define MILS       0     /* 0.001 inches */
39  #define MM         1     /* millimeters */
```

```
40  #define INCHES     2      /* inches      */
41  #define UM         3      /* micrometers */
42
43  #define MAXMEM     111        /* used to set databases to max memory */
44
45  #define FILESDIR   "FILES"
46  #define DATADIR    "DATA"
47
48  /* Mirror and Focus limits */
49  #define MINMIRROR (unsigned int)0
50  #define MAXMIRROR (unsigned int)65535
51  #define FOCUSINC 7            /* Focus controller minimum increment */
52
53  /* Part Translator Commands */
54  #define RESET           0
55  #define OVERPEDESTAL    1
56  #define OVERRETICLE     2
57  #define PARTTOPEDESTAL  3
58  #define PARTTORETICLE   4
59
60  #define ID_TIMER1  1                  /* timer id */
61
62  /********************************************************************/
63  /* Type Definitions                                                 */
64  /********************************************************************/
65  /* IWINDOW array indexes */
66  #define XLEFT      0
67  #define YTOP       1
68  #define XWIDTH     2
69  #define YHEIGHT    3
70  typedef BYTE IWINDOW[4];      /* image window type definition */
71
72  /********************************************************************/
73  /* Structure Definitions                                            */
74  /*    ***** All variable names below, begin with an Upper case character. */
75  /********************************************************************/
76
77  /* System Status Structure */
78  struct SYSTEMSTATUS
79  {
80      char SerialNo[80];        /* system serial number */
81      char Owner[80];           /* owner of the system */
82      float TotalHours;         /* total number of system operation hours */
83      long TotalCycles;         /* total number of inspection cycles */
84      long Cycles;              /* number of inspection cycles since the last start time */
85      long CalibCycles;         /* number of lifetime calibration cycles */
86      long NumberOfStarts;      /* number of times the program was started in its life time */
87      time_t InstallTime;       /* time and date system was installed */
88      time_t CalibPeriod;       /* time period between calibration expires */
89      time_t StartTime;         /* the time & date the system was last started */
90      int MirrorDelay;          /* milleseconds to allow mirrors to settle */
91      int FocusDelay;           /* milleseconds to allow focus to settle */
92      int LightsDelay;          /* milleseconds to allow lights to sette */
93      char FileDir[80];         /* directory where database files are */
94      char FileDrive[5];        /* drive     where database files are */
```

```
 95        char DataDir[80];          /* directory to put measurement data */
 96        char DataDrive[5];         /* drive     to put measurement data */
 97   }; /* end of struct SYSTEMSTATUS */
 98
 99   /* Part Coordinate Transformation Types */
100   #define IDENTITY        0
101   #define MINSKEW         1
102   #define MINTWEEZE       2
103   #define MINSKEWTWEEZE   3
104   #define ANSI            4
105
106   /* Inspection Settings Structure */
107   struct INSPSETTINGS
108   {
109        BOOL ManualMode;           /* Manual step through inspection cycle */
110        BOOL EngData;              /* Engineering data file or not */
111        char EngFilename[40];      /* Engineering data file name */
112        int  CyclesPerPart;        /* number of inspection cycles per part */

113        BYTE PartCoordTransType;   /* part coordinate transform type */
114   }; /* end of INSPSETTINGS */
115
116   /* Object Attributes Structure */
117   struct OBJECTATTR
118   {
119        /* full-pixel info */
120        /* The full-pixel edge is parallel to the width of the detection window */
121        int FPixMinCont;           /* minimum edge contrast for detection */
122        int FPixWidth;             /* width of window to use, in pixels */
123
124        /* sub-pixel info */
125        /* The sub-pixel edge is perpendicular to the height of the detection window */
126        int SPixMinCont;           /* minimum edge contrast for detection */
127        /* the size of the sub-pixel detection window */
128        int SPixShortDim;          /* width  of window, in pixels */
129        int SPixLongDim;           /* height of window, in pixels */
130   }; /* end of struct OBJECTATTR */
131
132   /* Statistics Structure                                                 */
133   /* To eliminate precision errors, the values must be normalized, using the */
134   /* first value. The first value is stored in variable Mean, until the mean*/
135   /* is calculated.                                                       */
136   /*                                                                      */
137   /* If (N==1) then Mean = first value                                    */
138   /* Sum    = Sum + Value - Mean     **** Note: Remember Mean = first value */
139   /* Sum2   = Sum2 + (Value - Mean)*(Value - Mean)                        */
140   /* Mean   = Sum / N + Mean                                              */
141   /* StdDev = SQRT((Sum2 - Sum*Sum / N)/(N-1))                            */
142   struct STATS
143   {
144        unsigned int N;            /* number of samples */
145        float Sum;                 /* sum of the values */
146        float Sum2;                /* sum of the values squared */
147        float Mean;                /* computed mean of the values */
148                                   /* also used to store the first value */
149        float StdDev;              /* standard deviation */
```

```
150   }; /* end of struct STAT */
151
152   /*******************/
153   /* PART database */
154   /*******************/
155
156   #define PRIMARY    0            /* perspective types */
157   #define SECONDARY  1
158
159   /* Perspective Structure */
160   struct PERSPECT
161   {
162       IWINDOW SearchWin;          /* object search window, image coords */
163       BYTE ScanIndex;             /* object perspective from this scan index */
164       BYTE ViewIndex;             /* view index of the scan */
165       float Position[VECT2];      /* object position, image coords */
166       float Dimension[VECT2];     /* object dimensions, image coords */
167       struct STATS PosStat[VECT2];/* position statistics */
168       struct STATS DimStat[VECT2];/* dimension statistics */
169   }; /* end of structure PERSPECT */
170
171   /* Float World Coordinate Structure */
172   struct FWORLD
173   {
174       float Position[VECT3];      /* world position:x,y,z */
175       float Dimension[VECT3];     /* world dimensions:x,y,z */
176   }; /* end of struct FWORLD */
177
178   /* Double World Coordinate Structure */
179   struct DWORLD
180   {
181       double Position[VECT3];     /* world position:x,y,z */
182       double Dimension[VECT3];    /* world dimensions:x,y,z */
183   }; /* end of struct DWORLD */
184
185   /* World Statistics Structure */
186   struct WORLDSTATS
187   {
188       struct STATS Position[VECT3];  /* position statistics */
189       struct STATS Dimension[VECT3]; /* dimension statistics */
190   }; /* end of WORLDSTATS struct */
191
192   /* maxnimum number of perspectives of each object */
193   #define MAXPERSPECTS 2
194   /* object types */
195   #define GWLEAD_PX       0
196   #define GWLEAD_NX       1
197   #define GWLEAD_PY       2
198   #define GWLEAD_NY       3
199   #define GWCORN_PXPY     4
200   #define GWCORN_PXNY     5
201   #define GWCORN_NXPY     6
202   #define GWCORN_NXNY     7
203   #define GWCORN_PYPX     8
204   #define GWCORN_PYNX     9
```

```
205  #define GWCORN_NYPX          10
206  #define GWCORN_NYNX          11
207  #define GWCENT_DOUBLE_PX     12
208  #define GWCENT_DOUBLE_NX     13
209  #define GWCENT_DOUBLE_PY     14
210  #define GWCENT_DOUBLE_NY     15
211  #define GWCENT_SINGLE_PX     16
212  #define GWCENT_SINGLE_NX     17
213  #define GWCENT_SINGLE_PY     18
214  #define GWCENT_SINGLE_NY     19
215  #define BLACK_CIRCLE         20
216  #define EDGE_WB_X_PN         21
217  #define EDGE_WB_X_NP         22
218  #define EDGE_WB_Y_PN         23
219  #define EDGE_WB_Y_NP         24
220
221  /* Object Structure */
222  struct OBJECT
223  {
224      BYTE Type;                          /* object type */
225      char Label[LABELSIZE];              /* object label */
226      char Status;                        /* object status */
227      struct DWORLD World;                /* object world coordinates */
228      struct DWORLD Part;                 /* object part coordinates */
229      struct FWORLD Ideal;                /* object ideal part coordinates */
230      struct WORLDSTATS WorldStats;       /* object world coordinate statistics */
231      BYTE NumberOfPerspects;             /* Number of viewing perspectives */
232      struct PERSPECT Perspect[MAXPERSPECTS]; /* Viewing perspective info */
233  }; /* end of struct OBJECT */
234
235  /* maxnimum number of objects in a group */
236  #define MAXOBJECTS 60
237  /* Grup types, used in object groups and measure groups */
238  #define SIDE1       0
239  #define SIDE2       1
240  #define SIDE3       2
241  #define SIDE4       3
242  #define PARTLOCATE  4
243
244  /* Group Structure */
245  struct GROUP
246  {
247      BYTE Type;                          /* group type */
248      char Label[LABELSIZE];              /* group label */
249      char Status;                        /* group status */
250      struct DWORLD World;                /* group world coordinates */
251      struct DWORLD Part;                 /* group part coordinates */
252      struct FWORLD Ideal;                /* group ideal part coordinates */
253      BYTE NumberOfObjects;               /* Number of Objects in Group */
254      HANDLE ObjectH[MAXOBJECTS];         /* Array of memory Handles */
255      /* Array of far pointers to objects of a group */
256      struct OBJECT far *ObjectPtr[MAXOBJECTS];
257  }; /* end of struct GROUP */
258
```

```
259  /* maximum number of groups of objects in the part */
260  #define MAXGROUPS    5
261  #define OFPPRT       1         /* part types */
262
263  /* Part Structure */
264  struct PART
265  {
266      BYTE Type;                            /* part type */
267      BYTE UnitType;                        /* unit type */
268      char Label[LABELSIZE];                /* part label */
269      char Status;                          /* part status */
270      double PartToWorld[ROW3][COL3];       /* Part To World Transformation Matrix */
271      double WorldToPart[ROW3][COL3];       /* World To Part Transformation Matrix */
272      struct DWORLD World;                  /* part world coordinates */
273      float Rotation;                       /* rotation of part on World coords */
274      BYTE NumberOfGroups;                  /* Number Object Groups in the Part */
275      HANDLE GroupH[MAXGROUPS];             /* Array of memory handles */
276      /* array of far pointers to the groups */
277      struct GROUP far *GroupPtr[MAXGROUPS];
278  }; /* end of struct PART */
279
280  /*********************/
281  /* MOTION database */
282  /*********************/
283
284  /* max objects per view */
285  #define MAXOBJECTSVIEW  10
286
287  /* View structure */
288  struct VIEW
289  {
290      BYTE Type;                            /* view type = scan type=OPI */
291      char Label[LABELSIZE];                /* view label */
292      unsigned int Mirror[VECT2];           /* mirror position x&y, 0-65535 */
293      unsigned int Focus;                   /* focus position, 0-65535 */
294      float OpticalPathLength;              /* distances from optical origin to viewplane */
295      double ViewPoint[VECT3];              /* (x,y,z) world position of viewplane */
296      double ViewUnit[VECT3][VECT3];        /* viewplane orientation, u,v,w unit vectors */
297      double ViewDim[VECT3];                /* dimensions of the view plane */
298      BYTE NumberOfObjects;                 /* number of objects in this view */
299      BYTE GroupIndex[MAXOBJECTSVIEW];      /* group index of object in view */
300      BYTE ObjectIndex[MAXOBJECTSVIEW];     /* object index of object in view */
301      BYTE PerspectIndex[MAXOBJECTSVIEW];   /* perspective index of object in view */
302  }; /* end of struct VIEW */
303
304  /* max views per scan  */
305  #define MAXVIEWS        20
306  /* Scan types */
307  /* The scan types are also used in optical path types */
308  /* The scan types = view types = OpticalPathIndex    */
309  /* The optical path index is an index into the ModelPtr->OpticalPath[] array */
310  #define BOTTOM_VIEW 0
311  #define SIDE_NX     1
312  #define SIDE_NY     2
```

```
313 #define SIDE_PX     3
314 #define SIDE_PY     4
315
316 /* scan structure */
317 struct SCAN
318 {
319     BYTE Type;                      /* type of scan=view type=OPI */
320     char Label[LABELSIZE];          /* scan label */
321     BYTE LightSetting;              /* light setting for the scan */
322     BYTE NumberOfViews;             /* number of views in the scan */
323     HANDLE ViewH[MAXVIEWS];         /* Array of memory handles */
324     struct VIEW far *ViewPtr[MAXVIEWS];/* array pointers to views of a scan */
325 }; /* end of struct SCAN */
326
327 /* max scans per motion database */
328 #define MAXSCANS    9
329 /* motion type */
330 #define QFPMTN      1
331
332 /* motion structure */
333 struct MOTION
334 {
335     BYTE Type;                      /* type of motion */
336     BYTE UnitType;                  /* unit type */
337     char Label[LABELSIZE];          /* motion label */
338     BYTE NumberOfScans;             /* number of scans made by the motion */
339     HANDLE ScanH[MAXSCANS];         /* Array of memory handles */
340     struct SCAN far *ScanPtr[MAXSCANS]; /* pointer to the scan */
341 }; /* end of struct MOTION */
342
343 /*******************/
344 /* MODEL Database */
345 /*******************/
346
347 /* Focus Model Structure */
348 struct FOCUSMODEL
349 {
350     /* polynomial coefficients used to compute V of the ViewDim vector */
351     /*      from the focus position                                    */
352     float CoeffV[VECT3];
353     /* polynomial coefficients used to compute W of the ViewDim vector */
354     /*      from the focus position                                    */
355     float CoeffW[VECT3];
356     /* polynomial coefficients used to compute the optical path length(opl) */
357     /*      from the focus position                                    */
358     float CoeffOPL[VECT3];
359 }; /* end of struct FOCUSMODEL */
360
361 /* X & Y Mirror Model structure */
362 struct MIRRORMODEL
363 {
364     /* polynomial coefficients to compute mirror angles from mirror position */
365     float Coeff[VECT3];
366 }; /* end of struct MIRRORMODEL */
367
```

```
368  /* indexes into the Surface array */
369  #define XMIRROR        1        /* X moveable mirror */
370  #define YMIRROR        2        /* Y moveable mirror */
371  #define DUSTBOT        3        /* Dust cover glass plate, bottom */
372  #define DUSTTOP        4        /* Dust cover glass plate, top */
373  #define RETICLEBOT     5        /* Reticle glass plate, bottom */
374  #define RETICLETOP     6        /* Reticle glass plate, top */
375  #define PXMIRROR       7        /* positive x side mirror */
376  #define PYMIRROR       8        /* positive y side mirror */
377  #define NXMIRROR       9        /* negative x side mirror */
378  #define NYMIRROR       10       /* negative y side mirror */
379
380  /* surface types */
381  #define ORIGIN         0    /* also used for an index to the Surface array */
382  #define REFLECT        1
383  #define REFRACT        2
384
385  /* Optical Surface structure */
386  struct SURFACE
387  {
388      BYTE Type;                      /* surface type: REFLECT, REFRACT */
389      char Label[LABELSIZE];          /* surface label */
390      float RefractiveIndex;          /* refractive index, past the surface */
391      double Position[VECT3];         /* world surface position */
392      /* unit world vector normal to the surface anchored at the position vector */
393      double Normal[VECT3];
394  }; /* end of struct SURFACE */
395
396  /* maximum number of surfaces in the model and per optical path */
397  #define MAXSURFACES    11
398
399  /* maximum number of optical path in the model */
400  #define MAXOPTICALPATHES 5
401
402  /* Optical Path Structure                    */
403  /* an optical path is a ordered list of surfaces */
404  /* optical path types are the same as scan types */
405  struct OPTICALPATH
406  {
407      BYTE Type;                      /* optical path type */
408      char Label[LABELSIZE];          /* optical path label */
409      BYTE LightSwitches;             /* bits to turn for lights */
410      BYTE NumberOfSurfaces;          /* number of surfaces along the path */
411      BYTE SurfaceIndex[MAXSURFACES]; /* array of indexes to the surfaces */
412      /* array of pointers to the surfaces in the optical path */
413      struct SURFACE far *SurfacePtr[MAXSURFACES]; /* not dynamically allocated */
414  }; /* end of struct OPTICALPATH */
415
416  /* Model types */
417  #define QFPMDL         1
418
419  /* Model structure */
420  struct MODEL
```

```
421  {
422      BYTE  Type;                          /* model type */
423      BYTE  UnitType;                      /* unit type */
424      char  Label[LABELSIZE];              /* model label */
425      time_t CalibTime;                    /* last time & date the system was calibrated */
426      BYTE  NumberOfSurfaces;              /* number of different surfaces in model */
427      struct SURFACE Surface[MAXSURFACES]; /* array of surfaces */
428      BYTE  NumberOfPathes;                /* number of different pathes in model */
429      /* array of optical pathes */
430      struct OPTICALPATH OpticalPath[MAXOPTICALPATHES];
431      /* the unit vectors u,v,w that define the view plane at the optical origin */
432      double OriginViewUnit[VECT3][VECT3];
433      /* angle between OriginViewVector u and x axis world vector(1,0,0) */
434      float CameraRollAngle;
435      /* the ratio of ViewDim[U]/ViewDim[V]; assumed constant for all views */
436      double AspectRatio;
437      struct FOCUSMODEL FocusModel;        /* structure discribing focus */
438      struct MIRRORMODEL MirrorModel[VECT2]; /* x & y moving mirror models */
439  }; /* end of struct MODEL */
440
441  /**********************/
442  /* MEASUREMENT Database */
443  /**********************/
444
445  /* maximum number of objects used in a measurment */
446  #define MAXOBJECTSPERMEASURE    2
447  /* maximum number of different sort criteria that can be used */
448  #define MAXSORTS    2
449
450  /* Measurement Structure */
451  struct MEASURE
452  {
453      BYTE  Type;                          /* measurement type, same as MeasGroup */
454      char  Label[LABELSIZE];              /* measurment label */
455      int   Status;                        /* measurement status */
456      float Value;                         /* the value of the measure */
457      BOOL  Passed[MAXSORTS];              /* did measurement pass, TRUE/FALSE */
458      struct STATS Stats;                  /* measurment statistics */
459      BYTE  NumberOfObjects;               /* number of object used in this measure */
460      /* index to the group of objects */
461      BYTE  GroupIndex[MAXOBJECTSPERMEASURE];
462      /* index to the objects used in this measure */
463      BYTE  ObjectIndex[MAXOBJECTSPERMEASURE];
464  }; /* end of struct MEASURE */
465
466  /* Maximum number of measures per group */
467  #define MAXMEASURES    MAXOBJECTS
468
469  /* Measurement Group Structure */
470  struct MEASGROUP
471  {
472      BYTE  Type;                          /* measurement type, same as MeasType */
473      char  Label[LABELSIZE];              /* measurment group label */
474      int   Status;                        /* measurement group status */
475      BOOL  Passed[MAXSORTS];              /* did measurement group pass, TRUE/FALSE */
```

```
476     struct STATS Stats;         /* measurment stats for this measure group */
477     BYTE  MinIndex;             /* index to the measure with the min value */
478     BYTE  MaxIndex;             /* index to the measure with the max value */
479     BYTE  NumberOfMeasures;     /* number of measures in this group */
480     /* array of memory handles to measurements */
481     HANDLE MeasureH[MAXMEASURES];
482     /* array of memory pointer to measurements */
483     struct MEASURE far *MeasurePtr[MAXMEASURES];
484 ); /* end of struct MEASGROUP */
485
486 /* Maximum number of measurement groups per type */
487 #define MAXMEASGROUPS    4    /* one group for each side */
488 /* Measurement class types */
489 #define SKEW          0
490 #define TWEEZE        1
491 #define COP           2
492 #define LEADWIDTH     3
493 #define LEADTIPTOTIP  4
494 #define BODYX         5
495 #define BODYY         6
496 #define POSX          7
497 #define POSY          8
498 #define ROTATE        9
499
500 /* Measurement Class Structure */
501 struct MEASCLASS
502 {
503     BYTE  Type;                 /* measurement class type */
504     char  Label[LABELSIZE];     /* measurment type label */
505     float Nominal;              /* nominal value for this measurement type */
506     BOOL  TestTol[MAXSORTS];    /* indicates whether measurement is tested */
507     float MinTol[MAXSORTS];     /* minimum tolerance value */
508     float MaxTol[MAXSORTS];     /* maximum tolerance value */
509     int   Status;               /* measurement type status */
510     BOOL  Passed[MAXSORTS];     /* did measurement type pass, TRUE/FALSE */
511     struct STATS Stats;         /* measurment stats for this measure type */
512     BYTE  MinIndex;             /* index to the group with the min measure */
513     BYTE  MaxIndex;             /* index to the group with the max measure */
514     BYTE  NumberOfGroups;       /* number of groups of measures of this type */
515     /* array of memory handles to measurement groups */
516     HANDLE MeasGroupH[MAXMEASGROUPS];
517     /* array of memory pointer to measurement groups */
518     struct MEASGROUP far *MeasGroupPtr[MAXMEASGROUPS];
519 ); /* end of struct MEASCLASS */
520
521 /* part numbering orientation, clockwise and counter-clockwise */
522 #define CW   0
523 #define CCW  1
524
525 /* Part Lead Numbering Structure */
526 struct NUMBERING
527 {
528     int   TotalLeads;           /* total number of leads on the part */
529     BYTE  Orientation;          /* Clockwise(CW) or Counter Clock Wise(CCW) */
530     int   NumberOfLeads[4];     /* number of leads on each side */
```

```
531     int FirstLead[4];              /* Lead number of first lead on side */
532     int LastLead[4];               /* Lead number of last  lead on side */
533 }; /* end of struct NUMBERING */
534
535 /* Ideal Part Definition Structure */
536 struct IDEALPART
537 {
538     float Body[VECT3];             /* world body dimensions (x,y,z) */
539     float StandOff;                /* the package stand off height */
540     float LeadPitch;               /* the lead pitch */
541     float LeadThick;               /* lead thickness(height) */
542     float LeadFoot;                /* length of the lead foot */
543     float LeadUpperRad;            /* Radius of the lead upper bend */
544     float LeadLowerRad;            /* Radius of the lead lower bend */
545     float LeadFootAngle;           /* angle of the foot */
546     float LeadWidth;               /* width of the lead */
547     float LeadExitHeight;          /* height where lead exits the body */
548     float LeadTipTip[VECT2];       /* lead tip to tip in x,y direction */
549     struct NUMBERING Numbering;    /* lead number information */
550 }; /* end of struct IDEALPART */
551
552 /* Maximum number of measurements classes in the measurement database */
553 #define MAXMEASCLASSES         10
554 /* Measurement database types */
555 #define QFPMEAS                1
556
557 /* Measurement Database Structure */
558 struct MEASDBASE
559 {
560     BYTE Type;                     /* type of measurement database */
561     BYTE UnitType;                 /* unit type */
562     char Label[LABELSIZE];         /* measurement database label */
563     int Status;                    /* status of measurement database */
564     struct IDEALPART IdealPart;    /* measurments of an ideal part */
565     BYTE NumberOfSorts;            /* number of different sort criteria */
566     BOOL Passed[MAXSORTS];         /* has current part passed, TRUE/FALSE */
567     int NoSorted[MAXSORTS];        /* number of parts of a lot in each sort */
568     int NoFailed;                  /* number of parts of a lot that failed all sorts */
569     int TotalNo;                   /* total number of parts in the lot */
570     BYTE NumberOfClasses;          /* number of different measurment classes */
571     /* array of memory handles for different measurement classes */
572     HANDLE MeasClassH[MAXMEASCLASSES];
573     /* array of memory pointers for different measurement classes */
574     struct MEASCLASS far *MeasClassPtr[MAXMEASCLASSES];
575 }; /* end of MEASDBASE */
576
577 /* Lot Information structure */
578 struct LOTINFO
579 {
580     char LotNo[80];                /* Lot number */
581     char Description[80];          /* Lot description */
582     char Operator[80];             /* Operator */
583 }; /* end of struct LOTINFO */
584
```

```
585  /***********************************************************/
586  /* Global Variables                                         */
587  /***********************************************************/
588  extern double PI;                 /* geometric constant PI */
589  extern float CycleTime;           /* part inspection loop time , sec */
590
591  /* Global Indexes into the databases */
592  extern BYTE GGroup;               /* global current group index */
593  extern BYTE GObject;              /* global current object index */
594  extern BYTE GPerspect;            /* global current perspective index */
595  extern BYTE GScan;                /* global current scan index */
596  extern BYTE GView;                /* global current view index */
597  extern BYTE GViewObject;          /* global current view object */
598
599  /* System Flags */
600  extern BOOL PartSelected;
601  extern BOOL Calibrated;
602
603  extern BOOL DisplayImages;
604  extern BOOL DisplayGraphics;
605  extern BOOL DisplayMaxValues;
606  extern BOOL DisplayTolerances;
607  extern BOOL LotStatistics;
608
609  extern BOOL AdvancedOptions;
610  extern BOOL DebugGraphics;
611  extern BOOL DebugData;
612  extern BOOL LongFiles;
613  extern BOOL ObjectStats;
614  extern BOOL DefineParts;
615  extern BOOL Motion;
616  extern BOOL Lights;
617  extern BOOL AcquireImages;
618  extern BOOL ProcessImages;
619  extern BOOL Assume2a;
620  extern BOOL NoPoaZa;
621  extern BOOL Translator;
622  extern BOOL AppInit;              /* has ApplicationInit() been called */
623
624
625  /* Database handles and pointers */
626  extern HANDLE          PartH;     /* memory handle to Part database */
627  extern struct PART     far *PartPtr;  /* pointer to Part database */
628  extern HANDLE          MotionH;   /* memory handle to Motion database */
629  extern struct MOTION   far *MotionPtr;/* pointer to Motion database */
630  extern HANDLE          ModelH;    /* memory handle to Model database */
631  extern struct MODEL    far *ModelPtr; /* pointer to the Model database */
632  extern HANDLE          MeasH;     /* memory handle to Measurement database */
633  extern struct MEASDBASE far *MeasPtr; /* pointer to the Measurement database */
634
635  #define MAXBUFS      1            /* maximum number of image buffers */
636  #define BUF0         0            /* image buffers */
637  #define BUF1         1
638  extern HANDLE   ImageH[MAXBUFS];  /* memory handles to image buffers */
```

```
639  extern BYTE far *ImagePtr[MAXBUFS]; /* pointers to image buffers */
640
641  extern struct SYSTEMSTATUS SystemStatus;
642  extern struct INSPSETTINGS InspSettings;
643  extern struct OBJECTATTR   ObjectAttr;
644  extern struct LOTINFO      LotInfo;
645
646  /*********** end of module qfp.h ****************************************/

1  /************************************************************************
  2
  3      Module Name: Model.c
  4
  5      Software Copyright (C) 1991
  6      Scanner Technologies Corp., MPLS, MN. All Rights Reserved.
  7
  8      Description: This module contains functions that operate on or with
  9          the MODEL database. The Model refers to the model of the Cyclops
 10          inspection system.
 11
 12      List of Functions:
 13          AllocModel()
 14          LockModel()
 15          UnlockModel()
 16          FreeModel()
 17          DefaultModel()
 18          DefaultOpticalPath()
 19          DefaultSurface()
 20          StoreModel(char far *filename)
 21          LoadModel(char far *filename)
 22          BLD_LoadModelDlgProc(hDlg, message, wParam, lParam)
 23          BLD_LoadModelDlgFunc(hWnd, message, wParam, lParam)
 24          BLD_StoreModelDlgProc(hDlg, message, wParam, lParam)
 25          BLD_StoreModelDlgFunc(hWnd, message, wParam, lParam)
 26          ComputeViewPlane(struct SCAN far *scanPtr, struct VIEW far *view)
 27          ComputeViewPoint(struct VIEW far *viewPtr)
 28          CompViewDim(struct VIEW far *viewPtr)
 29          CompMirrorSurfaces(struct VIEW far *viewPtr)
 30          SurfaceAndRayPoint()
 31          ReflectRay(double far *ray, struct SURFACE far *surfacePtr)
 32          RefractRay(double far *ray, struct SURFACE far *isurfacePtr,
 33              struct SURFACE far *tsurfacePtr))
 34          ComputeMirrorFromVP(struct VIEW far *viewPtr)
 35          ComputeViewsFromObjects()
 36
 37      Notes:
 38
 39  ************************************************************************/
 40  #include "STC.H"              /* company info */
 41  static char *model = COPYRIGHT;  /* embedded copyright notice */
 42
 43  #include <WINDOWS.H>          /* Microsoft header file */
 44  #include <string.h>           /* Microsoft string functions header file */
 45  #include <stdlib.h>           /* Microsoft standard functions header file */
 46  #include <stdio.h>            /* Microsoft standard io functions header file */
 47  #include <io.h>               /* Microsoft file i/o header file */
 48  #include <time.h>             /* Microsoft time functions header file */
```

```
 49    #include <float.h>         /* Microsoft floating point   fxmacros */
 50    #include <math.h>          /* Microsoft math functions header file */
 51    #include "QFP_WM.H"        /* header file generated by WindowsMaker */
 52    #include "MODEL.WMC"       /* header file generated by WindowsMaker */
 53    #include "Default.h"       /* some general macro definitions */
 54    #include "QFP.H"           /* the main header file for the QFP application */
 55    #include "PROTO.H"         /* function prototypes */
 56
 57    /******************************************************************
 58
 59        Function Name: DefaultModel()
 60
 61        Engineer: Steve Palm
 62
 63        Revision History:
 64            Created              19:05:12 Tue 19-Mar-1991
 65
 66        Description: This function will free currently allocated Model memory,
 67            allocate new Model memory, and fill variables with default data.
 68
 69        Call Syntax: error = DefaultModel(type);
 70
 71        Argument Declarations Within Function:
 72            BYTE type;          / Model type to generate default data /
 73
 74        Returns: error = OK,        successful
 75                       = ERROR1,    unable to free previously allocate Model memory.
 76                       = ERROR2,    unable to allocate Model memory.
 77                       = ERROR3,    unable to set default Scan data.
 78
 79        Notes or Special Conditions:
 80
 81    ******************************************************************/
 82    int DefaultModel(BYTE type)
 83    {
 84        int error;              /* error return code */
 85
 86        /* if Model has been previously allocated, free the Model memory */
 87        if (ModelH != NULL)
 88        {
 89            error = freeModel();
 90            if (error != OK) return(ERROR1);
 91        } /* end of if */
 92
 93        /* Allocate new Model memory */
 94        error = AllocModel();
 95        if (error != OK) return(ERROR2);
 96
 97        /* set default model data */
 98        ModelPtr->Type              = type;
 99        ModelPtr->UnitType          = MILS;
100        _fstrcpy(ModelPtr->Label, "DEFAULT");
101        ModelPtr->CalibTime         = 0;
102        DefaultSurfaces();
103        DefaultOpticalPathes();
```

```
104
105         ModelPtr->OriginViewUnit[U][X]    = (double)1.0;
106         ModelPtr->OriginViewUnit[U][Y]    = (double)0.0;
107         ModelPtr->OriginViewUnit[U][Z]    = (double)0.0;
108         ModelPtr->OriginViewUnit[V][X]    = (double)0.0;
109         ModelPtr->OriginViewUnit[V][Y]    = (double)0.0;
110         ModelPtr->OriginViewUnit[V][Z]    = (double)-1.0;
111         ModelPtr->OriginViewUnit[W][X]    = (double)0.0;
112         ModelPtr->OriginViewUnit[W][Y]    = (double)1.0;
113         ModelPtr->OriginViewUnit[W][Z]    = (double)0.0;
114         ModelPtr->CameraRollAngle         = (float)PI;
115         ModelPtr->AspectRatio             = (float)4.0/3.0;
116         ModelPtr->FocusModel.CoeffV[0]    = (float)50.0;
117         ModelPtr->FocusModel.CoeffV[1]    = (float)0.0;
118         ModelPtr->FocusModel.CoeffV[2]    = (float)0.0;
119         ModelPtr->FocusModel.CoeffW[0]    = FLT_MAX;
120         ModelPtr->FocusModel.CoeffW[1]    = (float)0.0;
121         ModelPtr->FocusModel.CoeffW[2]    = (float)0.0;
122         ModelPtr->FocusModel.CoeffOPL[0]  = (float)0.0;
123         ModelPtr->FocusModel.CoeffOPL[1]  = (float)0.0;
124         ModelPtr->FocusModel.CoeffOPL[2]  = (float)0.0;
125         ModelPtr->MirrorModel[X].Coeff[0] = (float)0.0;
126         ModelPtr->MirrorModel[X].Coeff[1] = (float)0.0;
127         ModelPtr->MirrorModel[X].Coeff[2] = (float)0.0;
128         ModelPtr->MirrorModel[Y].Coeff[0] = (float)0.0;
129         ModelPtr->MirrorModel[Y].Coeff[1] = (float)0.0;
130         ModelPtr->MirrorModel[Y].Coeff[2] = (float)0.0;
131
132         /* Which Model type to use */
133         switch(type)
134         {
135             /* GFP Model type */
136             case GFPMDL:
137                 /* Set default data to Model structure */
138                 break;
139
140             /* Maximum Memory Model type */
141             case MAXMEM:
142                 ModelPtr->Type = NULL;
143                 /* Set default data to Model structure */
144                 break;
145
146             /* unknown Model type */
147             default:
148                 /* Set default data to Model structure */
149                 break;
150
151         } /* end of switch(type) */
152
153         return(OK);
154     }
155 /*********** end of function DefaultModel() ******************************/
156
157 /************************************************************************
158
```

```
159     Function Name: DefaultSurfaces()
160
161     Engineer: Steve Palm
162
163     Revision History:
164         Created                 13:15:22 Mon 01-Apr-1991
165
166     Description: This function will fill in the model database with default
167         surface data.
168
169     Call Syntax: DefaultSurfaces()
170
171     Argument Declarations Within Function: none.
172
173     Returns: none.
174
175     Notes or Special Conditions:
176
177 ****************************************************************/
178 void DefaultSurfaces(void)
179 {
180     int surfIndex;                  /* index into the Surface array */
181
182     ModelPtr->NumberOfSurfaces = 11;
183
184     surfIndex = ORIGIN;
185     _fstrcpy(ModelPtr->Surface[surfIndex].Label,"ORIGIN");
186     ModelPtr->Surface[surfIndex].Type           = ORIGIN;
187     ModelPtr->Surface[surfIndex].RefractiveIndex = (float )  1.0;
188     ModelPtr->Surface[surfIndex].Position[X]    = (double)-1378.0;
189     ModelPtr->Surface[surfIndex].Position[Y]    = (double) 2000.0;
190     ModelPtr->Surface[surfIndex].Position[Z]    = (double)13260.0;
191     ModelPtr->Surface[surfIndex].Normal[X]      = (double)    0.0;
192     ModelPtr->Surface[surfIndex].Normal[Y]      = (double)   -1.0;
193     ModelPtr->Surface[surfIndex].Normal[Z]      = (double)    0.0;
194
195     surfIndex = XMIRROR;
196     _fstrcpy(ModelPtr->Surface[surfIndex].Label,"XMIRROR");
197     ModelPtr->Surface[surfIndex].Type           = REFLECT;
198     ModelPtr->Surface[surfIndex].RefractiveIndex = (float )1.0;
199     ModelPtr->Surface[surfIndex].Position[X]    = (double)-1378.0;
200     ModelPtr->Surface[surfIndex].Position[Y]    = (double)   0.0;
201     ModelPtr->Surface[surfIndex].Position[Z]    = (double)13260.0;
202     ModelPtr->Surface[surfIndex].Normal[X]      = cos(DegToRad(45.0));
203     ModelPtr->Surface[surfIndex].Normal[Y]      = cos(DegToRad(45.0));
204     ModelPtr->Surface[surfIndex].Normal[Z]      = (double)   0.0;
205
206     surfIndex = YMIRROR;
207     _fstrcpy(ModelPtr->Surface[surfIndex].Label,"YMIRR");
208     ModelPtr->Surface[surfIndex].Type           = REFLECT;
209     ModelPtr->Surface[surfIndex].RefractiveIndex = (float )1.0;
210     ModelPtr->Surface[surfIndex].Position[X]    = (double)0.0;
211     ModelPtr->Surface[surfIndex].Position[Y]    = (double)0.0;
212     ModelPtr->Surface[surfIndex].Position[Z]    = (double)13260.0;
213     ModelPtr->Surface[surfIndex].Normal[X]      = cos(DegToRad(135.0));
```

```
214    ModelPtr->Surface[surfIndex].Normal[Y]      = (double)0.0;
215    ModelPtr->Surface[surfIndex].Normal[Z]      = cos(DegToRad(135.0));
216
217    surfIndex = DUSTBOT;
218    _fstrcpy(ModelPtr->Surface[surfIndex].Label,"DustBot");
219    ModelPtr->Surface[surfIndex].Type            = REFRACT;
220    ModelPtr->Surface[surfIndex].RefractiveIndex = (float )1.516;
221    ModelPtr->Surface[surfIndex].Position[X]     = (double)0.0;
222    ModelPtr->Surface[surfIndex].Position[Y]     = (double)0.0;
223    ModelPtr->Surface[surfIndex].Position[Z]     = (double)1250.0;
224    ModelPtr->Surface[surfIndex].Normal[X]       = (double)0.0;
225    ModelPtr->Surface[surfIndex].Normal[Y]       = (double)0.0;
226    ModelPtr->Surface[surfIndex].Normal[Z]       = (double)1.0;
227
228    surfIndex = DUSTTOP;
229    _fstrcpy(ModelPtr->Surface[surfIndex].Label,"DustTop");
230    ModelPtr->Surface[surfIndex].Type            = REFRACT;
231    ModelPtr->Surface[surfIndex].RefractiveIndex = (float )1.0;
232    ModelPtr->Surface[surfIndex].Position[X]     = (double)0.0;
233    ModelPtr->Surface[surfIndex].Position[Y]     = (double)0.0;
234    ModelPtr->Surface[surfIndex].Position[Z]     = (double)1000.0;
235    ModelPtr->Surface[surfIndex].Normal[X]       = (double)0.0;
236    ModelPtr->Surface[surfIndex].Normal[Y]       = (double)0.0;
237    ModelPtr->Surface[surfIndex].Normal[Z]       = (double)-1.0;
238
239    surfIndex = RETICLEBOT;
240    _fstrcpy(ModelPtr->Surface[surfIndex].Label,"RtclBot");
241    ModelPtr->Surface[surfIndex].Type            = REFRACT;
242    ModelPtr->Surface[surfIndex].RefractiveIndex = (float )1.516;
243    ModelPtr->Surface[surfIndex].Position[X]     = (double)0.0;
244    ModelPtr->Surface[surfIndex].Position[Y]     = (double)0.0;
245    ModelPtr->Surface[surfIndex].Position[Z]     = (double)250.0;
246    ModelPtr->Surface[surfIndex].Normal[X]       = (double)0.0;
247    ModelPtr->Surface[surfIndex].Normal[Y]       = (double)0.0;
248    ModelPtr->Surface[surfIndex].Normal[Z]       = (double)1.0;
249
250    surfIndex = RETICLETOP;
251    _fstrcpy(ModelPtr->Surface[surfIndex].Label,"RtclTop");
252    ModelPtr->Surface[surfIndex].Type            = REFRACT;
253    ModelPtr->Surface[surfIndex].RefractiveIndex = (float )1.0;
254    ModelPtr->Surface[surfIndex].Position[X]     = (double)0.0;
255    ModelPtr->Surface[surfIndex].Position[Y]     = (double)0.0;
256    ModelPtr->Surface[surfIndex].Position[Z]     = (double)0.0;
257    ModelPtr->Surface[surfIndex].Normal[X]       = (double)0.0;
258    ModelPtr->Surface[surfIndex].Normal[Y]       = (double)0.0;
259    ModelPtr->Surface[surfIndex].Normal[Z]       = (double)-1.0;
260
261    surfIndex = PXMIRROR;
262    _fstrcpy(ModelPtr->Surface[surfIndex].Label,"PXMIRROR");
263    ModelPtr->Surface[surfIndex].Type            = REFLECT;
264    ModelPtr->Surface[surfIndex].RefractiveIndex = (float )1.0;
265    ModelPtr->Surface[surfIndex].Position[X]     = (double)1900.0;
266    ModelPtr->Surface[surfIndex].Position[Y]     = (double)0.0;
267    ModelPtr->Surface[surfIndex].Position[Z]     = (double)0.0;
268    ModelPtr->Surface[surfIndex].Normal[X]       = cos(DegToRad(134.5));
```

```
269       ModelPtr->Surface[surfIndex].Normal[Y]      = (double)0.0;
270       ModelPtr->Surface[surfIndex].Normal[Z]      = cos(DegToRad(44.5));
271
272       surfIndex = PYMIRROR;
273       _fstrcpy(ModelPtr->Surface[surfIndex].Label,"PYMIRROR");
274       ModelPtr->Surface[surfIndex].Type           = REFLECT;
275       ModelPtr->Surface[surfIndex].RefractiveIndex = (float )1.0;
276       ModelPtr->Surface[surfIndex].Position[X]    = (double)0.0;
277       ModelPtr->Surface[surfIndex].Position[Y]    = (double)1900.0;
278       ModelPtr->Surface[surfIndex].Position[Z]    = (double)0.0;
279       ModelPtr->Surface[surfIndex].Normal[X]      = (double)0.0;
280       ModelPtr->Surface[surfIndex].Normal[Y]      = cos(DegToRad(134.5));
281       ModelPtr->Surface[surfIndex].Normal[Z]      = cos(DegToRad(44.5));
282
283       surfIndex = NXMIRROR;
284       _fstrcpy(ModelPtr->Surface[surfIndex].Label,"NXMIRROR");
285       ModelPtr->Surface[surfIndex].Type           = REFLECT;
286       ModelPtr->Surface[surfIndex].RefractiveIndex = (float )1.0;
287       ModelPtr->Surface[surfIndex].Position[X]    = (double)-1900.0;
288       ModelPtr->Surface[surfIndex].Position[Y]    = (double)0.0;
289       ModelPtr->Surface[surfIndex].Position[Z]    = (double)0.0;
290       ModelPtr->Surface[surfIndex].Normal[X]      = cos(DegToRad(45.5));
291       ModelPtr->Surface[surfIndex].Normal[Y]      = (double)0.0;
292       ModelPtr->Surface[surfIndex].Normal[Z]      = cos(DegToRad(44.5));
293
294       surfIndex = NYMIRROR;
295       _fstrcpy(ModelPtr->Surface[surfIndex].Label,"NYMIRROR");
296       ModelPtr->Surface[surfIndex].Type           = REFLECT;
297       ModelPtr->Surface[surfIndex].RefractiveIndex = (float )1.0;
298       ModelPtr->Surface[surfIndex].Position[X]    = (double)0.0;
299       ModelPtr->Surface[surfIndex].Position[Y]    = (double)-1900.0;
300       ModelPtr->Surface[surfIndex].Position[Z]    = (double)0.0;
301       ModelPtr->Surface[surfIndex].Normal[X]      = (double)0.0;
302       ModelPtr->Surface[surfIndex].Normal[Y]      = cos(DegToRad(45.5));
303       ModelPtr->Surface[surfIndex].Normal[Z]      = cos(DegToRad(44.5));
304
305       return;
306   }
307   /*********** end of function DefaultSurfaces() ****************************/
308
309   /****************************************************************************
310
311       Function Name: DefaultOpticalPathes()
312
313       Engineer: Steve Palm
314
315       Revision History:
316           Created                 13:18:15 Mon 01-Apr-1991
317
318       Description: This function will fill the model with default optical
319           path data.
320
321       Call Syntax: DefaultOpticalPathes()
322
323       Argument Declarations Within Function: none.
324
```

```
325      Returns: none.
326
327      Notes or Special Conditions:
328
329  ******************************************************************/
330  void DefaultOpticalPathes(void)
331  {
332      int optIndex;              /* index into the optical path array */
333      BYTE surfIndex;            /* index into the Surface array */
334      int surface;               /* surface number in optical path */
335
336      ModelPtr->NumberOfPathes = 5;
337
338      optIndex = BOTTOM_VIEW;
339      ModelPtr->OpticalPath[optIndex].Type            = BOTTOM_VIEW;
340      _fstrcpy(ModelPtr->OpticalPath[optIndex].Label,"BOTVIEW");
341      ModelPtr->OpticalPath[optIndex].LightSwitches   = 0x20;  /* bit 5 */
342      ModelPtr->OpticalPath[optIndex].NumberOfSurfaces = 5;
343          surface  = 0;
344          surfIndex = ORIGIN;
345              ModelPtr->OpticalPath[optIndex].SurfaceIndex[surface] = surfIndex;
346              ModelPtr->OpticalPath[optIndex].SurfacePtr  [surface] =
347                  &ModelPtr->Surface[surfIndex];
348          surface++;
349          surfIndex = XMIRROR;
350              ModelPtr->OpticalPath[optIndex].SurfaceIndex[surface] = surfIndex;
351              ModelPtr->OpticalPath[optIndex].SurfacePtr  [surface] =
352                  &ModelPtr->Surface[surfIndex];
353          surface++;
354          surfIndex = YMIRROR;
355              ModelPtr->OpticalPath[optIndex].SurfaceIndex[surface] = surfIndex;
356              ModelPtr->OpticalPath[optIndex].SurfacePtr  [surface] =
357                  &ModelPtr->Surface[surfIndex];
358          surface++;
359          surfIndex = RETICLEBOT;
360              ModelPtr->OpticalPath[optIndex].SurfaceIndex[surface] = surfIndex;
361              ModelPtr->OpticalPath[optIndex].SurfacePtr  [surface] =
362                  &ModelPtr->Surface[surfIndex];
363          surface++;
364          surfIndex = RETICLETOP;
365              ModelPtr->OpticalPath[optIndex].SurfaceIndex[surface] = surfIndex;
366              ModelPtr->OpticalPath[optIndex].SurfacePtr  [surface] =
367                  &ModelPtr->Surface[surfIndex];
368
369      optIndex = SIDE_PX;
370      ModelPtr->OpticalPath[optIndex].Type            = SIDE_PX;
371      _fstrcpy(ModelPtr->OpticalPath[optIndex].Label,"SIDE_PX");
372      ModelPtr->OpticalPath[optIndex].LightSwitches   = 0x04;  /* bit 2 */
373      ModelPtr->OpticalPath[optIndex].NumberOfSurfaces = 4;
374          surface  = 0;
375          surfIndex = ORIGIN;
376              ModelPtr->OpticalPath[optIndex].SurfaceIndex[surface] = surfIndex;
377              ModelPtr->OpticalPath[optIndex].SurfacePtr  [surface] =
378                  &ModelPtr->Surface[surfIndex];
379          surface++;
```

```
380         surfIndex = XMIRROR;
381             ModelPtr->OpticalPath[optIndex].SurfaceIndex[surface] = surfIndex;
382             ModelPtr->OpticalPath[optIndex].SurfacePtr  [surface] =
383                 &ModelPtr->Surface[surfIndex];
384         surface++;
385         surfIndex = YMIRROR;
386             ModelPtr->OpticalPath[optIndex].SurfaceIndex[surface] = surfIndex;
387             ModelPtr->OpticalPath[optIndex].SurfacePtr  [surface] =
388                 &ModelPtr->Surface[surfIndex];
389         surface++;
390         surfIndex = PXMIRROR;
391             ModelPtr->OpticalPath[optIndex].SurfaceIndex[surface] = surfIndex;
392             ModelPtr->OpticalPath[optIndex].SurfacePtr  [surface] =
393                 &ModelPtr->Surface[surfIndex];
394
395     optIndex = SIDE_PY;
396     ModelPtr->OpticalPath[optIndex].Type          = SIDE_PY;
397     _fstrcpy(ModelPtr->OpticalPath[optIndex].Label,"SIDE_PY");
398     ModelPtr->OpticalPath[optIndex].LightSwitches   = 0x08; /* bit 3 */
399     ModelPtr->OpticalPath[optIndex].NumberOfSurfaces = 4;
400         surface   = 0;
401         surfIndex = ORIGIN;
402             ModelPtr->OpticalPath[optIndex].SurfaceIndex[surface] = surfIndex;
403             ModelPtr->OpticalPath[optIndex].SurfacePtr  [surface] =
404                 &ModelPtr->Surface[surfIndex];
405         surface++;
406         surfIndex = XMIRROR;
407             ModelPtr->OpticalPath[optIndex].SurfaceIndex[surface] = surfIndex;
408             ModelPtr->OpticalPath[optIndex].SurfacePtr  [surface] =
409                 &ModelPtr->Surface[surfIndex];
410         surface++;
411         surfIndex = YMIRROR;
412             ModelPtr->OpticalPath[optIndex].SurfaceIndex[surface] = surfIndex;
413             ModelPtr->OpticalPath[optIndex].SurfacePtr  [surface] =
414                 &ModelPtr->Surface[surfIndex];
415         surface++;
416         surfIndex = PYMIRROR;
417             ModelPtr->OpticalPath[optIndex].SurfaceIndex[surface] = surfIndex;
418             ModelPtr->OpticalPath[optIndex].SurfacePtr  [surface] =
419                 &ModelPtr->Surface[surfIndex];
420
421     optIndex = SIDE_NX;
422     ModelPtr->OpticalPath[optIndex].Type = SIDE_NX;
423     _fstrcpy(ModelPtr->OpticalPath[optIndex].Label,"SIDE_NX");
424     ModelPtr->OpticalPath[optIndex].LightSwitches   = 0x01; /* bit 0 */
425     ModelPtr->OpticalPath[optIndex].NumberOfSurfaces = 4;
426         surface   = 0;
427         surfIndex = ORIGIN;
428             ModelPtr->OpticalPath[optIndex].SurfaceIndex[surface] = surfIndex;
429             ModelPtr->OpticalPath[optIndex].SurfacePtr  [surface] =
430                 &ModelPtr->Surface[surfIndex];
431         surface++;
432         surfIndex = XMIRROR;
433             ModelPtr->OpticalPath[optIndex].SurfaceIndex[surface] = surfIndex;
434             ModelPtr->OpticalPath[optIndex].SurfacePtr  [surface] =
435                 &ModelPtr->Surface[surfIndex];
```

```
436         surface++;
437         surfIndex = YMIRROR;
438             ModelPtr->OpticalPath[optIndex].SurfaceIndex[surface] = surfIndex;
439             ModelPtr->OpticalPath[optIndex].SurfacePtr  [surface] =
440                 &ModelPtr->Surface[surfIndex];
441         surface++;
442         surfIndex = NXMIRROR;
443             ModelPtr->OpticalPath[optIndex].SurfaceIndex[surface] = surfIndex;
444             ModelPtr->OpticalPath[optIndex].SurfacePtr  [surface] =
445                 &ModelPtr->Surface[surfIndex];
446
447     optIndex = SIDE_NY;
448     ModelPtr->OpticalPath[optIndex].Type = SIDE_NY;
449     _fstrcpy(ModelPtr->OpticalPath[optIndex].Label,"SIDE_NY");
450     ModelPtr->OpticalPath[optIndex].LightSwitches    = 0x02; /* bit 1 */
451     ModelPtr->OpticalPath[optIndex].NumberOfSurfaces = 4;
452         surface  = 0;
453         surfIndex = ORIGIN;
454             ModelPtr->OpticalPath[optIndex].SurfaceIndex[surface] = surfIndex;
455             ModelPtr->OpticalPath[optIndex].SurfacePtr  [surface] =
456                 &ModelPtr->Surface[surfIndex];
457         surface++;
458         surfIndex = XMIRROR;
459             ModelPtr->OpticalPath[optIndex].SurfaceIndex[surface] = surfIndex;
460             ModelPtr->OpticalPath[optIndex].SurfacePtr  [surface] =
461                 &ModelPtr->Surface[surfIndex];
462         surface++;
463         surfIndex = YMIRROR;
464             ModelPtr->OpticalPath[optIndex].SurfaceIndex[surface] = surfIndex;
465             ModelPtr->OpticalPath[optIndex].SurfacePtr  [surface] =
466                 &ModelPtr->Surface[surfIndex];
467         surface++;
468         surfIndex = NYMIRROR;
469             ModelPtr->OpticalPath[optIndex].SurfaceIndex[surface] = surfIndex;
470             ModelPtr->OpticalPath[optIndex].SurfacePtr  [surface] =
471                 &ModelPtr->Surface[surfIndex];
472
473     return;
474 }
475 /********** end of function DefaultOpticalPathes() ********************/
476
477 /*************************************************************************
478
479     Function Name: ComputeViewPlane()
480
481     Engineer: Steve Palm
482
483     Revision History:
484         Created                 01:10:57 Sun 21-Apr-1991
485
486     Description: This function will compute the ViewPlane from the
487         mirror coordinates.
488
489     Call Syntax: error = CompViewPlane(struct VIEW far *viewPtr);
490
```

```
491    Argument Declarations Within Function:
492        struct VIEW far *viewPtr;      \ pointer to view info \
493
494    Returns: error = OK,       successful
495                  = ERROR1,    unsuccessful
496
497    Notes or Special Conditions:
498
499 ***********************************************************************/
500 int ComputeViewPlane(struct VIEW far *viewPtr)
501 {
502     BYTE surface;               /* the surface number in the optical path */
503     BYTE numberOfSurfaces;      /* number of surfaces in the optical path */
504     double distance;            /* distance between 2 points */
505     int error;                  /* function return code */
506     double surfacePoint[VECT3]; /* point on the surface */
507     float interimOPL;           /* the interim OpticalPathLength */
508     struct SURFACE far *surfacePtr; /* pointer to surface data */
509     int opi;                    /* local optical path index */
510
511     opi = viewPtr->Type;        /* the view type is the OpticalPathIndex */
512
513     /* compute ViewDim and OPL from Focus */
514     CompViewDim(viewPtr);
515     /* compute X & Y Mirror surface from Mirror coordinates */
516     CompMirrorSurfaces(viewPtr);
517     /* Initialize ViewPoint to Origin surface position */
518     CopyVectD3(viewPtr->ViewPoint, ModelPtr->Surface[ORIGIN].Position);
519     /* Set ViewUnit to the OriginViewUnit */
520     CopyVectD3(viewPtr->ViewUnit[U], ModelPtr->OriginViewUnit[U]);
521     CopyVectD3(viewPtr->ViewUnit[V], ModelPtr->OriginViewUnit[V]);
522     CopyVectD3(viewPtr->ViewUnit[W], ModelPtr->OriginViewUnit[W]);
523     interimOPL = (float)0.0;    /* initialize to 0 */
524     numberOfSurfaces = ModelPtr->OpticalPath[opi].NumberOfSurfaces;
525     /* bounce the ViewPlane through the optical path */
526     for (surface = 1; surface < numberOfSurfaces; surface++)
527     {
528         /* set the surface pointer */
529         surfacePtr = ModelPtr->OpticalPath[opi].SurfacePtr[surface];
530         /* The next surface point is intersection of ray ViewUnit[W] */
531         /*     and Surface[surface]                                  */
532         error = SurfaceAndRayPoint(viewPtr->ViewPoint, viewPtr->ViewUnit[W],
533                 surfacePtr, surfacePoint);
534         if (error != OK) return(ERROR1);
535         /* Compute distance between ViewPoint and surfacePoint      */
536         distance = DistVectD3(viewPtr->ViewPoint, surfacePoint);
537         /* if (interimOPL + distance) > OPL exit the loop           */
538         if ((interimOPL + (float)distance) > viewPtr->OpticalPathLength)
539             break;
540         /* Accumlate interimOPL, interimOPL += distance             */
541         interimOPL += (float)distance;
542         /* Refract or Reflect ViewUnit off the Surface              */
543         if (surfacePtr->Type == REFLECT)
544         {
545             ReflectRay(viewPtr->ViewUnit[U], surfacePtr);
```

```
546            ReflectRay(viewPtr->ViewUnit[V], surfacePtr);
547            ReflectRay(viewPtr->ViewUnit[W], surfacePtr);
548        }
549        else if (surfacePtr->Type == REFRACT)
550        {
551            /* To reflect, the refract. index must be known for  */
552            /*     incident[surface-1] surface and                */
553            /*     transmitted[surface] surface                   */
554            RefractRay(viewPtr->ViewUnit[U], ModelPtr->OpticalPath[opl].
555                SurfacePtr[surface-1], surfacePtr);
556            RefractRay(viewPtr->ViewUnit[V], ModelPtr->OpticalPath[opl].
557                SurfacePtr[surface-1], surfacePtr);
558            RefractRay(viewPtr->ViewUnit[W], ModelPtr->OpticalPath[opl].
559                SurfacePtr[surface-1], surfacePtr);
560        }
561
562        /* Set ViewPoint to the surface point */
563        CopyVectD3(viewPtr->ViewPoint, surfacePoint);
564
565    } /* end of surface loop */
566
567    /* Compute final ViewPoint */
568    distance = (double)(viewPtr->OpticalPathLength - interimOPL);
569    viewPtr->ViewPoint[X] -= distance*viewPtr->ViewUnit[W][X];
570    viewPtr->ViewPoint[Y] -= distance*viewPtr->ViewUnit[W][Y];
571    viewPtr->ViewPoint[Z] -= distance*viewPtr->ViewUnit[W][Z];
572
573    return(OK);
574 }
575 /*********** end of function ComputeViewPlane() ***********************/
576
577 /*******************************************************************
578
579     Function Name: ComputeViewPoint()
580
581     Engineer: Steve Palm
582
583     Revision History:
584         Created              15:47:42 Tue 23-Apr-1991
585
586     Description: This function will compute the ViewPoint from the
587         mirror coordinates.
588
589     Call Syntax: error = CompViewPlane(struct VIEW far *viewPtr);
590
591     Argument Declarations Within Function:
592         struct VIEW far *viewPtr;      \ pointer to view info \
593
594     Returns: error = OK,      successful
595                    = ERROR1,  unsuccessful
596
597     Notes or Special Conditions:
598
599 *******************************************************************/
600 int ComputeViewPoint(struct VIEW far *viewPtr)
```

```
601  {
602     BYTE surface;              /* the surface number in the optical path */
603     BYTE numberOfSurfaces;     /* number of surfaces in the optical path */
604     double distance;           /* distance between 2 points */
605     int error;                 /* function return code */
606     double surfacePoint[VECT3]; /* point on the surface */
607     float interimOPL;          /* the interim OpticalPathLength */
608     struct SURFACE far *surfacePtr; /* pointer to surface data */
609     int opi;                   /* local optical path index */
610
611     opi = viewPtr->Type;       /* the view type is the OpticalPathIndex */
612
613     /* compute ViewDim and OPL from Focus */
614     CompViewDim(viewPtr);
615     /* compute X & Y Mirror surface from Mirror coordinates */
616     CompMirrorSurfaces(viewPtr);
617     /* Initialize ViewPoint to Origin surface position */
618     CopyVectD3(viewPtr->ViewPoint, ModelPtr->Surface[ORIGIN].Position);
619     /* Set ViewUnit to the OriginViewUnit */
620     CopyVectD3(viewPtr->ViewUnit[W], ModelPtr->OriginViewUnit[W]);
621     interimOPL = (float)0.0;   /* initialize to 0 */
622     numberOfSurfaces = ModelPtr->OpticalPath[opi].NumberOfSurfaces;
623     /* bounce the ViewPlane through the optical path */
624     for (surface = 1; surface < numberOfSurfaces; surface++)
625     {
626         /* set the surface pointer */
627         surfacePtr = ModelPtr->OpticalPath[opi].SurfacePtr[surface];
628         /* The next surface point is intersection of ray ViewUnit[W] */
629         /*     and Surface[surface]                                  */
630         error = SurfaceAndRayPoint(viewPtr->ViewPoint, viewPtr->ViewUnit[W],
631                 surfacePtr, surfacePoint);
632         if (error != OK) return(ERROR1);
633         /* Compute distance between ViewPoint and surfacePoint       */
634         distance = DistVectD3(viewPtr->ViewPoint, surfacePoint);
635         /* If (interimOPL + distance) > OPL exit the loop            */
636         if ((interimOPL + (float)distance) > viewPtr->OpticalPathLength)
637             break;
638         /* Accumlate interimOPL, interimOPL += distance              */
639         interimOPL += (float)distance;
640         /* Refract or Reflect ViewUnit off the Surface               */
641         if (surfacePtr->Type == REFLECT)
642             ReflectRay(viewPtr->ViewUnit[W], surfacePtr);
643         else if (surfacePtr->Type == REFRACT)
644         {
645             /* To reflect, the refract. index must be known for */
646             /*     incident[surface-1] surface and              */
647             /*     transmitted[surface] surface                 */
648  /*         RefractRay(viewPtr->ViewUnit[U], ModelPtr->OpticalPath[opi].
649                 SurfacePtr[surface-1], surfacePtr);
650             RefractRay(viewPtr->ViewUnit[V], ModelPtr->OpticalPath[opi].
651                 SurfacePtr[surface-1], surfacePtr);
652             RefractRay(viewPtr->ViewUnit[W], ModelPtr->OpticalPath[opi].
653                 SurfacePtr[surface-1], surfacePtr);
654  */     }
655
```

```
656         /* Set ViewPoint to the surface point */
657         CopyVectD3(viewPtr->ViewPoint, surfacePoint);
658
659     } /* end of surface loop */
660
661     /* Compute final ViewPoint */
662     distance = (double)(viewPtr->OpticalPathLength - interimOPL);
663     viewPtr->ViewPoint[X] -= distance*viewPtr->ViewUnit[W][X];
664     viewPtr->ViewPoint[Y] -= distance*viewPtr->ViewUnit[W][Y];
665     viewPtr->ViewPoint[Z] -= distance*viewPtr->ViewUnit[W][Z];
666
667     return(OK);
668 }
669 /*********** end of function ComputeViewPoint() *************************/
670
671 /*************************************************************************
672
673     Function Name: CompViewDim()
674
675     Engineer: Steve Palm
676
677     Revision History:
678         Created                 01:33:05 Sun 21-Apr-1991
679
680     Description: This function will compute the ViewDim[] array and the
681         optical path length(OPL) from the model and the position of the
682         focus.
683
684     Call Syntax: CompViewDim(viewPtr)
685
686     Argument Declarations Within Function:
687         struct VIEW far *viewPtr;       \ pointer to view data \
688
689     Returns: none.
690
691     Notes or Special Conditions:
692
693 *************************************************************************/
694 void CompViewDim(struct VIEW far *viewPtr)
695 {
696     viewPtr->ViewDim[V] = (double)(ModelPtr->FocusModel.CoeffV[0] +
697                             ModelPtr->FocusModel.CoeffV[1] *
698                             (float)viewPtr->Focus);
699     viewPtr->ViewDim[U] = viewPtr->ViewDim[V] * ModelPtr->AspectRatio;
700     viewPtr->ViewDim[W] = (double)ModelPtr->FocusModel.CoeffW[0];
701     viewPtr->OpticalPathLength = ModelPtr->FocusModel.CoeffOPL[0] +
702                             ModelPtr->FocusModel.CoeffOPL[1] *
703                             (float)viewPtr->Focus;
704     return;
705 }
706 /*********** end of function CompViewDim() *****************************/
707
708 /*************************************************************************
709
710     Function Name: CompFocus()
711
```

```
712      Engineer: Steve Palm
713
714      Revision History:
715          Created                 01:33:05 Sun 21-Apr-1991
716
717      Description: This function will compute the Focus position from a
718          given Optical Path Length.  Uses the cooeficients in the Focus
719          Model.
720
721      Call Syntax: CompFocus(viewPtr)
722
723      Argument Declarations Within Function:
724          struct VIEW far *viewPtr;      \ pointer to view data \
725
726      Returns: none.
727
728      Notes or Special Conditions:
729
730  ******************************************************************/
731  void CompFocus(struct VIEW far *viewPtr)
732  {
733      float focus;       /* temporary focus holder */
734
735      focus = (viewPtr->OpticalPathLength - ModelPtr->FocusModel.CoeffOPL[0]) /
736                  ModelPtr->FocusModel.CoeffOPL[1];
737
738      /* check computed focus position for limits */
739      if     (focus < (float)MINMIRROR)
740          viewPtr->Focus = (unsigned int)MINMIRROR;
741      else if (focus > (float)MAXMIRROR)
742          viewPtr->Focus = (unsigned int)MAXMIRROR;
743      else
744          viewPtr->Focus = (unsigned int)(focus + (float)0.5);
745
746      return;
747  }
748  /*********** end of function CompFocus() ****************************/
749
750  /*******************************************************************
751
752      Function Name: CompMirrorSurfaces()
753
754      Engineer: Steve Palm
755
756      Revision History:
757          Created                 01:46:14 Sun 21-Apr-1991
758
759      Description: This function will compute the position and normal vectors
760          for the X and Y mirror surfaces, from the X & Y mirror positions
761          and the cooefficients in the model.
762
763      Call Syntax: CompMirrorSurfaces(viewPtr)
764
765      Argument Declarations Within Function:
766          struct VIEW far *viewPtr;      \ the pointer to the view data \
767
```

```
768         Returns: none.
769
770         Notes or Special Conditions:
771
772    ************************************************************************/
773    void CompMirrorSurfaces(struct VIEW far *viewPtr)
774    {
775         double angle;               /* computed angle */
776
777         /* compute the X Mirror Angle */
778         angle = (double)ModelPtr->MirrorModel[X].Coeff[0] +
779                 (double)ModelPtr->MirrorModel[X].Coeff[1] *
780                 (double)viewPtr->Mirror[X] +
781                 (double)ModelPtr->MirrorModel[X].Coeff[2] *
782                 (double)viewPtr->Mirror[Y];
783         /* Set the normal vector to the surface */
784         ModelPtr->Surface[XMIRROR].Normal[X] = cos(angle);
785         ModelPtr->Surface[XMIRROR].Normal[Y] = sin(angle);
786         ModelPtr->Surface[XMIRROR].Normal[Z] = (double)0.0;
787
788         /* compute the Y Mirror Angle */
789         angle = (double)ModelPtr->MirrorModel[Y].Coeff[0] +
790                 (double)ModelPtr->MirrorModel[Y].Coeff[1] *
791                 (double)viewPtr->Mirror[Y] +
792                 (double)ModelPtr->MirrorModel[Y].Coeff[2] *
793                 (double)viewPtr->Mirror[X];
794         /* Set the normal vector to the surface */
795         ModelPtr->Surface[YMIRROR].Normal[X] = cos(angle);
796         ModelPtr->Surface[YMIRROR].Normal[Y] = (double)0.0;
797         ModelPtr->Surface[YMIRROR].Normal[Z] = sin(angle);
798
799         return;
800    }
801    /*********** end of function CompMirrorSurfaces() *************************/
802
803    /**************************************************************************
804
805         Function Name: SurfaceAndRayPoint()
806
807         Engineer: Steve Palm
808
809         Revision History:
810              created             03:32:44 Sun 21-Apr-1991
811
812         Description: This function will compute the point that is at the
813              intersection of a ray and a surface.  A point on the ray must
814              also be given.
815
816         Call Syntax: error = SurfaceAndRayPoint(rayPoint, ray,
817                                      surfacePtr, surfacePoint)
818
819         Argument Declarations Within function:
820              double far rayPoint[VECT3];      / point on the ray /
821              double far ray[VECT3];           / the ray, must be unit vector /
822              struct SURFACE far *surfacePtr;  / the surface /
```

```
823         double far surfacePoint;        / the surface point to compute /
824
825     Returns: error = OK,        success
826                   = ERROR1     ray and normal to surface have 0 mag.
827                   = ERROR2     the ray has magnitude 0.
828
829     Notes or Special Conditions:
830
831 **********************************************************************/
832 int SurfaceAndRayPoint(double far rayPoint[VECT3], double far ray[VECT3],
833 struct SURFACE far *surfacePtr, double far surfacePoint[VECT3])
834 {
835     double denominator;
836     double d;
837     double numerator;
838
839     /* compute the denominator */
840     denominator = DotProduct(ray, surfacePtr->Normal);
841     if (denominator == (double)0.0) return(ERROR1);
842
843     /* plane equation: d = a*x + b*y + c*z, where d = a*x0 + b*y0 + c*z0 */
844     d = DotProduct(surfacePtr->Position, surfacePtr->Normal);
845
846     /* check for 0's in the ray unit vector */
847     if (ray[X] != (double)0.0)
848     {
849         numerator = ray[X]*d -
850                     (surfacePtr->Normal[Y]*(rayPoint[Y]*ray[X] - rayPoint[X]*ray[Y]) +
851                      surfacePtr->Normal[Z]*(rayPoint[Z]*ray[X] - rayPoint[X]*ray[Z]));
852         surfacePoint[X] = numerator / denominator;
853         surfacePoint[Y] = rayPoint[Y] + ray[Y] / ray[X] * (surfacePoint[X] - rayPoint[X]);
854         surfacePoint[Z] = rayPoint[Z] + ray[Z] / ray[X] * (surfacePoint[X] - rayPoint[X]);
855     }
856     else if (ray[Y] != (double)0.0)
857     {
858         numerator = ray[Y]*d -
859                     (surfacePtr->Normal[X]*(rayPoint[X]*ray[Y] - rayPoint[Y]*ray[X]) +
860                      surfacePtr->Normal[Z]*(rayPoint[Z]*ray[Y] - rayPoint[Y]*ray[Z]));
861         surfacePoint[Y] = numerator / denominator;
862         surfacePoint[X] = rayPoint[X] + ray[X] / ray[Y] * (surfacePoint[Y] - rayPoint[Y]);
863         surfacePoint[Z] = rayPoint[Z] + ray[Z] / ray[Y] * (surfacePoint[Y] - rayPoint[Y]);
864     }
865     else if (ray[Z] != (double)0.0)
866     {
867         numerator = ray[Z]*d -
868                     (surfacePtr->Normal[X]*(rayPoint[X]*ray[Z] - rayPoint[Z]*ray[X]) +
869                      surfacePtr->Normal[Y]*(rayPoint[Y]*ray[Z] - rayPoint[Z]*ray[Y]));
870         surfacePoint[Z] = numerator / denominator;
871         surfacePoint[X] = rayPoint[X] + ray[X] / ray[Z] * (surfacePoint[Z] - rayPoint[Z]);
872         surfacePoint[Y] = rayPoint[Y] + ray[Y] / ray[Z] * (surfacePoint[Z] - rayPoint[Z]);
873     }
874     else
875         return(ERROR2);    /* the magnitude of ray unit vector is 0! */
876
877     return(OK);
878 }
```

```
879  /********** end of function SurfaceAndRayPoint() ****************************/
880
881  /*******************************************************************************
882
883      Function Name: ReflectRay()
884
885      Engineer: Steve Palm
886
887      Revision History:
888          Created         04:21:02 Sun 21-Apr-1991
889
890      Description: This function will compute the reflected ray from
891          a surface.  The equation for reflecting a ray came from BYTE
892          Dec 1990, page 266.
893              R = V +2Nd, where d = -(V dot N)
894                  V = incident vector
895                  N = normal to the surface vector
896                  R = reflected vector
897
898      Call Syntax: Reflect(viewUnit, surfacePtr)
899
900      Argument Declarations Within Function:
901          double far *ray;
902          struct SURFACE far *surfacePtr;
903
904      Returns: none.
905
906      Notes or Special Conditions:
907
908  *******************************************************************************/
909  void ReflectRay(double far *ray, struct SURFACE far *surfacePtr)
910  {
911      double d;
912
913      d = (double)-2.0*DotProduct(ray, surfacePtr->Normal);
914      *(ray++) += surfacePtr->Normal[X] * d;
915      *(ray++) += surfacePtr->Normal[Y] * d;
916      *(ray--) += surfacePtr->Normal[Z] * d;
917      UnitVect3D(--ray);
918      return;
919  }
920  /********** end of function ReflectRay() *************************************/
921
922  /*******************************************************************************
923
924      Function Name: RefractRay()
925
926      Engineer: Steve Palm
927
928      Revision History:
929          Created                 11:14:20 Tue 23-Apr-1991
930
931      Description: This function will compute the refracted ray through
932          a surface.  The equation for refracting a ray came from BYTE
933          Dec 1990, page 266.
```

```
934              T = n*V + b*N
935                  V = the incident vector
936                  N = the surface normal vector
937                  T = the transmitted vector
938                  n = ni / nt
939                  ni = refractive index of the incident medium
940                  nt = refractive index of the transmitted medium
941                  b = (n*c - SQRT(a))
942                  c = -(V dot N)
943                  a = 1 + n*n(c*c-1)
944
945          NOTE: if (a<0) the incident ray is reflected not transmitted.
946
947      Call Syntax: error = Reflect(viewUnit, surfacePtr)
948
949      Argument Declarations Within Function:
950          double far *ray;                    \ the incident ray \
951          struct SURFACE far *isurfacePtr;    \ the incident surface \
952          struct SURFACE far *tsurfacePtr;    \ the transmitted surface \
953
954      Returns: error = OK,          everything OK
955                     = ERROR1,      The vector is reflected not refracted.
956                                    No operation performed on the vector.
957
958      Notes or Special Conditions:
959          If it is determined that the ray will not be transmitted,
960              an error will be returned.
961
962  ****************************************************************/
963  int RefractRay(double far *ray, struct SURFACE far *isurfacePtr,
964      struct SURFACE far *tsurfacePtr)
965  {
966      double c;
967      double n;
968      double a;
969      double b;
970
971      c = (double)-DotProduct(ray, tsurfacePtr->Normal);
972      n = isurfacePtr->RefractiveIndex / tsurfacePtr->RefractiveIndex;
973      a = 1 + n*n*(c*c-1);
974      /* check if the ray will be reflected */
975      if (a < (double)0) return(ERROR1);
976      b = (n*c - sqrt(a));
977
978      *ray = *(ray++) * n + a * tsurfacePtr->Normal[X];
979      *ray = *(ray++) * n + a * tsurfacePtr->Normal[Y];
980      *ray = *(ray--) * n + a * tsurfacePtr->Normal[Z];
981
982      UnitVect3D(--ray);
983      return(OK);
984  }
985  /*********** end of function RefractRay() *******************************/
986
987  /********************************************************************
988
```

```
989      Function Name: ComputeMirrorsFromVP()
990
991      Engineer: Steve Palm
992
993      Revision History:
994          Created by a human      16:12:21 Tue 23-Apr-1991
995
996      Description: This function will compute the Mirror and Focus coordinates
997          from the ViewPoint. The solution is obtained numerically.
998
999      Call Syntax: error = ComputeMirrorFromVP(viewPtr)
1,000
1,001    Argument Declarations Within function:
1,002        struct VIEW far *viewPtr;      / pointer to the View info /
1,003
1,004    Returns: error = OK,        success
1,005                   = ERROR1,    invalid view type, opi
1,006                   = ERROR2,    unable to compute better seed coords
1,007
1,008    Notes or Special Conditions:
1,009
1,010 ************************************************************************/
1,011 int ComputeMirrorFromVP(struct VIEW far *viewPtr, BOOL interactive)
1,012 {
1,013     double idealPoint[VECT3];      /* the ideal View Point */
1,014     double d1, d2, d3;             /* distances used to find mirror coords */
1,015     float minOPL=(float)0.0;       /* minimum optical path length */
1,016     BOOL moved;                    /* used to indicate when done */
1,017     BOOL inc;                      /* should the position be incremented */
1,018     unsigned int incCount;         /* used to increment the position */
1,019     unsigned int savedCount;       /* used to see if mirror or focus has moved */
1,020     char string[40];               /* used to display values in dialog box */
1,021     int maxCount = 35;             /* maximum numer of characters to place in string */
1,022     double value;                  /* value used to read numbers from dialog */
1,023     int error;                     /* function return value */
1,024     int surface;                   /* surface number in optical path */
1,025     int numberOfSurfaces;          /* number of surfaces in optical path */
1,026     struct SURFACE far *prevSurfPtr;/* pointer to previous surface */
1,027     struct SURFACE far *nextSurfPtr;/* pointer to next    surface */
1,028     int opi;                       /* optical path index */
1,029
1,030     /* Read the Ideal View Point from the dialog box or use ViewPoint */
1,031     /* The values read from the dialog box will have less precision */
1,032     if (interactive && MotionDatahDlg)
1,033     {
1,034         error = MessageBox(MotionDatahDlg, "Read Ideal View Point from dialog box? ",
1,035             "COMPUTE MIRRORS FROM VIEW POINT", MB_YESNOCANCEL);
1,036         if (error == IDCANCEL) return(OK);
1,037         if (error == IDYES)
1,038         {
1,039             GetDlgItemText(MotionDatahDlg, IDD_VPX, string, maxCount);
1,040             if (sscanf(string, "%lf", &value) > 0)
1,041                 viewPtr->ViewPoint[X] = value;
1,042             GetDlgItemText(MotionDatahDlg, IDD_VPY, string, maxCount);
1,043             if (sscanf(string, "%lf", &value) > 0)
```

```
1,044                   viewPtr->ViewPoint[Y] = value;
1,045               GetDlgItemText(MotionDatahDlg, IDD_VPZ, string, maxCount);
1,046               if (sscanf(string, "%lf", &value) > 0)
1,047                   viewPtr->ViewPoint[Z] = value;
1,048           }
1,049       } /* end of if dialog box */
1,050
1,051       /* If not Bottom View, compute the minimum optical path length */
1,052       /*     from the position of the surfaces on the optical path   */
1,053       if (viewPtr->Type != BOTTOM_VIEW)
1,054       {
1,055           surface = 0;
1,056           opi = viewPtr->Type;
1,057           if ((BYTE)opi >= ModelPtr->NumberOfPathes) return(ERROR1);
1,058           minOPL = (float)0.0;
1,059           numberOfSurfaces = ModelPtr->OpticalPath[opi].NumberOfSurfaces;
1,060           nextSurfPtr = ModelPtr->OpticalPath[opi].SurfacePtr[surface];
1,061           for (surface = 1; surface < numberOfSurfaces; surface++)
1,062           {
1,063               prevSurfPtr = nextSurfPtr;
1,064               nextSurfPtr = ModelPtr->OpticalPath[opi].SurfacePtr[surface];
1,065               minOPL += DistVectD3(prevSurfPtr->Position, nextSurfPtr->Position);
1,066           } /* end of surface loop */
1,067       } /* end of if BOTTOM_VIEW */
1,068
1,069       /* Get the ideal View Point and store locally */
1,070       CopyVectD3(idealPoint, viewPtr->ViewPoint);
1,071
1,072       /* used to run through the sequence again with a better starting point */
1,073       RETRY:
1,074
1,075       /* loop until the mirrors and focus are position whithin 1 count */
1,076       moved = TRUE;
1,077       while(moved)
1,078       {
1,079           /*********************/
1,080           /* Adjust the focus */
1,081           /*********************/
1,082           savedCount = viewPtr->Focus;
1,083           incCount = (unsigned int)(FOCUSINC*2*2*2*2*2*2*2);
1,084           while (incCount >= FOCUSINC)
1,085           {
1,086               if (viewPtr->Focus < MINMIRROR+incCount)
1,087                   viewPtr->Focus = MINMIRROR;
1,088               else
1,089                   viewPtr->Focus -= incCount;
1,090               ComputeViewPoint(viewPtr);
1,091               d1 = DistVectD3(idealPoint, viewPtr->ViewPoint);
1,092               if (viewPtr->Focus > MAXMIRROR-incCount)
1,093                   viewPtr->Focus = MAXMIRROR;
1,094               else
1,095                   viewPtr->Focus += incCount;
1,096               ComputeViewPoint(viewPtr);
1,097               d2 = DistVectD3(idealPoint, viewPtr->ViewPoint);
1,098               if (viewPtr->Focus > MAXMIRROR-incCount)
```

```
1,099              viewPtr->Focus = MAXMIRROR;
1,100          else
1,101              viewPtr->Focus += incCount;
1,102          ComputeViewPoint(viewPtr);
1,103          d3 = DistVectD3(idealPoint, viewPtr->ViewPoint);
1,104          viewPtr->Focus -= incCount;
1,105          /* Should the focus be incremented to get closer to the ideal point */
1,106          if (d1 < d2) inc = FALSE;
1,107          else         inc = TRUE;
1,108          /* Increment the focus until it is within a count. */
1,109          /* d2 will be smaller than d1 and d3 when finished. */
1,110          while(!(d1 >= d2 && d2 <= d3))
1,111          {
1,112              if (inc)
1,113              {
1,114                  /* increment focus to get closer to ideal point */
1,115                  if (viewPtr->Focus > MAXMIRROR-incCount)
1,116                      viewPtr->Focus = MAXMIRROR;
1,117                  else
1,118                      viewPtr->Focus += incCount;
1,119                  d1 = d2;
1,120                  d2 = d3;
1,121                  if (viewPtr->Focus > MAXMIRROR-incCount)
1,122                      viewPtr->Focus = MAXMIRROR;
1,123                  else
1,124                      viewPtr->Focus += incCount;
1,125                  ComputeViewPoint(viewPtr);
1,126                  d3 = DistVectD3(idealPoint, viewPtr->ViewPoint);
1,127                  viewPtr->Focus -= incCount;
1,128              } /* end of increment focus */
1,129              else
1,130              {
1,131                  /* decrement focus to get closer to ideal point */
1,132                  if (viewPtr->Focus < MINMIRROR+incCount)
1,133                      viewPtr->Focus = MINMIRROR;
1,134                  else
1,135                      viewPtr->Focus -= incCount;
1,136                  d3 = d2;
1,137                  d2 = d1;
1,138                  if (viewPtr->Focus < MINMIRROR+incCount)
1,139                      viewPtr->Focus = MINMIRROR;
1,140                  else
1,141                      viewPtr->Focus -= incCount;
1,142                  ComputeViewPoint(viewPtr);
1,143                  d1 = DistVectD3(idealPoint, viewPtr->ViewPoint);
1,144                  viewPtr->Focus += incCount;
1,145              } /* end of decrement focus */
1,146
1,147              if (viewPtr->Focus <= MINMIRROR) break;
1,148              if (viewPtr->Focus >= MAXMIRROR) break;
1,149          } /* end of while d2 is not the smallest */
1,150
1,151          /* display values in dialog box */
1,152          if (interactive && MotionDatahDlg)
1,153          {
```

```
1,154            sprintf(string, "%5u", viewPtr->Mirror[X]);
1,155               SetDlgItemText(MotionDatahDlg, IDD_XMIRROR, string);
1,156            sprintf(string, "%5u", viewPtr->Mirror[Y]);
1,157               SetDlgItemText(MotionDatahDlg, IDD_YMIRROR, string);
1,158            sprintf(string, "%5u", viewPtr->Focus);
1,159               SetDlgItemText(MotionDatahDlg, IDD_FOCUS, string);
1,160            sprintf(string, "%12.4E", viewPtr->ViewPoint[X]);
1,161               SetDlgItemText(MotionDatahDlg, IDD_VPX, string);
1,162            sprintf(string, "%12.4E", viewPtr->ViewPoint[Y]);
1,163               SetDlgItemText(MotionDatahDlg, IDD_VPY, string);
1,164            sprintf(string, "%12.4E", viewPtr->ViewPoint[Z]);
1,165               SetDlgItemText(MotionDatahDlg, IDD_VPZ, string);
1,166            sprintf(string, "%12.4E", viewPtr->OpticalPathLength);
1,167               SetDlgItemText(MotionDatahDlg, IDD_OPL, string);
1,168         } /* end of if dialog box */
1,169
1,170         incCount /= (unsigned int)2;
1,171      } /* end of while incCount */
1,172      /* check if focus has moved */
1,173      if (viewPtr->Focus != savedCount) moved = TRUE;
1,174      else                              moved = FALSE;
1,175
1,176      /***********************/
1,177      /* Adjust the Xmirror */
1,178      /***********************/
1,179      savedCount = viewPtr->Mirror[X];
1,180      incCount = (unsigned int)(1*2*2*2*2*2*2*2);
1,181      while (incCount >= 1)
1,182      {
1,183         if (viewPtr->Mirror[X] < MINMIRROR+incCount)
1,184            viewPtr->Mirror[X] = MINMIRROR;
1,185         else
1,186            viewPtr->Mirror[X] -= incCount;
1,187         ComputeViewPoint(viewPtr);
1,188         d1 = DistVectD3(idealPoint, viewPtr->ViewPoint);
1,189         if (viewPtr->Mirror[X] > MAXMIRROR-incCount)
1,190            viewPtr->Mirror[X] = MAXMIRROR;
1,191         else
1,192            viewPtr->Mirror[X] += incCount;
1,193         ComputeViewPoint(viewPtr);
1,194         d2 = DistVectD3(idealPoint, viewPtr->ViewPoint);
1,195         if (viewPtr->Mirror[X] > MAXMIRROR-incCount)
1,196            viewPtr->Mirror[X] = MAXMIRROR;
1,197         else
1,198            viewPtr->Mirror[X] += incCount;
1,199         ComputeViewPoint(viewPtr);
1,200         d3 = DistVectD3(idealPoint, viewPtr->ViewPoint);
1,201         viewPtr->Mirror[X] -= incCount;
1,202         /* Should the Xmirror be incremented to get closer to the ideal point */
1,203         if (d1 < d2) inc = FALSE;
1,204         else         inc = TRUE;
1,205         /* Increment the Xmirror until it is within a count. */
1,206         /* d2 will be smaller than d1 and d3 when finished. */
1,207         while(!(d1 >= d2 && d2 <= d3))
1,208         {
```

```
1,209        if (inc)
1,210        {
1,211            /* increment Xmirror to get closer to ideal point */
1,212            if (viewPtr->Mirror[X] > MAXMIRROR-incCount)
1,213                viewPtr->Mirror[X] = MAXMIRROR;
1,214            else
1,215                viewPtr->Mirror[X] += incCount;
1,216            d1 = d2;
1,217            d2 = d3;
1,218            if (viewPtr->Mirror[X] > MAXMIRROR-incCount)
1,219                viewPtr->Mirror[X] = MAXMIRROR;
1,220            else
1,221                viewPtr->Mirror[X] += incCount;
1,222            ComputeViewPoint(viewPtr);
1,223            d3 = DistVectD3(idealPoint, viewPtr->ViewPoint);
1,224            viewPtr->Mirror[X] -= incCount;
1,225        } /* end of increment Xmirror */
1,226        else
1,227        {
1,228            /* decrement Xmirror to get closer to ideal point */
1,229            if (viewPtr->Mirror[X] < MINMIRROR+incCount)
1,230                viewPtr->Mirror[X] = MINMIRROR;
1,231            else
1,232                viewPtr->Mirror[X] -= incCount;
1,233            d3 = d2;
1,234            d2 = d1;
1,235            if (viewPtr->Mirror[X] < MINMIRROR+incCount)
1,236                viewPtr->Mirror[X] = MINMIRROR;
1,237            else
1,238                viewPtr->Mirror[X] -= incCount;
1,239            ComputeViewPoint(viewPtr);
1,240            d1 = DistVectD3(idealPoint, viewPtr->ViewPoint);
1,241            viewPtr->Mirror[X] += incCount;
1,242        } /* end of decrement Xmirror */
1,243
1,244        if (viewPtr->Mirror[X] <= MINMIRROR) break;
1,245        if (viewPtr->Mirror[X] >= MAXMIRROR) break;
1,246    } /* end of while d2 is not the smallest */
1,247
1,248    /* display values in dialog box */
1,249    if (interactive && MotionDatahDlg)
1,250    {
1,251        sprintf(string, "%5u", viewPtr->Mirror[X]);
1,252            SetDlgItemText(MotionDatahDlg, IDD_XMIRROR, string);
1,253        sprintf(string, "%12.4E", viewPtr->ViewPoint[X]);
1,254            SetDlgItemText(MotionDatahDlg, IDD_VPX, string);
1,255        sprintf(string, "%12.4E", viewPtr->ViewPoint[Y]);
1,256            SetDlgItemText(MotionDatahDlg, IDD_VPY, string);
1,257        sprintf(string, "%12.4E", viewPtr->ViewPoint[Z]);
1,258            SetDlgItemText(MotionDatahDlg, IDD_VPZ, string);
1,259        sprintf(string, "%12.4E", viewPtr->OpticalPathLength);
1,260            SetDlgItemText(MotionDatahDlg, IDD_OPL, string);
1,261    } /* end of if dialog box */
1,262
1,263    incCount /= (unsigned int)2;
```

```
1,264        } /* end of while incCount */
1,265        /* check if Xmirror has moved */
1,266        if (viewPtr->Mirror[X] != savedCount) moved = TRUE;
1,267
1,268
1,269        /************************/
1,270        /* Adjust the Ymirror */
1,271        /************************/
1,272        savedCount = viewPtr->Mirror[Y];
1,273        incCount = (unsigned int)(1*2*2*2*2*2*2*2);
1,274        while (incCount >= 1)
1,275        {
1,276            if (viewPtr->Mirror[Y] < MINMIRROR+incCount)
1,277                viewPtr->Mirror[Y] = MINMIRROR;
1,278            else
1,279                viewPtr->Mirror[Y] -= incCount;
1,280            ComputeViewPoint(viewPtr);
1,281            d1 = DistVectD3(idealPoint, viewPtr->ViewPoint);
1,282            if (viewPtr->Mirror[Y] > MAXMIRROR-incCount)
1,283                viewPtr->Mirror[Y] = MAXMIRROR;
1,284            else
1,285                viewPtr->Mirror[Y] += incCount;
1,286            ComputeViewPoint(viewPtr);
1,287            d2 = DistVectD3(idealPoint, viewPtr->ViewPoint);
1,288            if (viewPtr->Mirror[Y] > MAXMIRROR-incCount)
1,289                viewPtr->Mirror[Y] = MAXMIRROR;
1,290            else
1,291                viewPtr->Mirror[Y] += incCount;
1,292            ComputeViewPoint(viewPtr);
1,293            d3 = DistVectD3(idealPoint, viewPtr->ViewPoint);
1,294            viewPtr->Mirror[Y] -= incCount;
1,295            /* Should the Ymirror be incremented to get closer to the ideal point */
1,296            if (d1 < d2) inc = FALSE;
1,297            else         inc = TRUE;
1,298            /* Increment the Ymirror until it is within a count. */
1,299            /* d2 will be smaller than d1 and d3 when finished. */
1,300            while(!(d1 >= d2 && d2 <= d3))
1,301            {
1,302                if (inc)
1,303                {
1,304                    /* Increment Ymirror to get closer to ideal point */
1,305                    if (viewPtr->Mirror[Y] > MAXMIRROR-incCount)
1,306                        viewPtr->Mirror[Y] = MAXMIRROR;
1,307                    else
1,308                        viewPtr->Mirror[Y] += incCount;
1,309                    d1 = d2;
1,310                    d2 = d3;
1,311                    if (viewPtr->Mirror[Y] > MAXMIRROR-incCount)
1,312                        viewPtr->Mirror[Y] = MAXMIRROR;
1,313                    else
1,314                        viewPtr->Mirror[Y] += incCount;
1,315                    ComputeViewPoint(viewPtr);
1,316                    d3 = DistVectD3(idealPoint, viewPtr->ViewPoint);
1,317                    viewPtr->Mirror[Y] -= incCount;
1,318                } /* end of increment Ymirror */
```

```
1,319              else
1,320              {
1,321                  /* decrement Ymirror to get closer to ideal point */
1,322                  if (viewPtr->Mirror[Y] < MINMIRROR+incCount)
1,323                      viewPtr->Mirror[Y] = MINMIRROR;
1,324                  else
1,325                      viewPtr->Mirror[Y] -= incCount;
1,326                  d3 = d2;
1,327                  d2 = d1;
1,328                  if (viewPtr->Mirror[Y] < MINMIRROR+incCount)
1,329                      viewPtr->Mirror[Y] = MINMIRROR;
1,330                  else
1,331                      viewPtr->Mirror[Y] -= incCount;
1,332                  ComputeViewPoint(viewPtr);
1,333                  d1 = DistVectD3(idealPoint, viewPtr->ViewPoint);
1,334                  viewPtr->Mirror[Y] += incCount;
1,335              } /* end of decrement Ymirror */
1,336
1,337              if (viewPtr->Mirror[Y] <= MINMIRROR) break;
1,338              if (viewPtr->Mirror[Y] >= MAXMIRROR) break;
1,339          } /* end of while d2 is not the smallest */
1,340
1,341          /* display values in dialog box */
1,342          if (interactive && MotionDatahDlg)
1,343          {
1,344              sprintf(string, "%5u", viewPtr->Mirror[Y]);
1,345                  SetDlgItemText(MotionDatahDlg, IDD_YMIRROR, string);
1,346              sprintf(string, "%12.4E", viewPtr->ViewPoint[X]);
1,347                  SetDlgItemText(MotionDatahDlg, IDD_VPX, string);
1,348              sprintf(string, "%12.4E", viewPtr->ViewPoint[Y]);
1,349                  SetDlgItemText(MotionDatahDlg, IDD_VPY, string);
1,350              sprintf(string, "%12.4E", viewPtr->ViewPoint[Z]);
1,351                  SetDlgItemText(MotionDatahDlg, IDD_VPZ, string);
1,352              sprintf(string, "%12.4E", viewPtr->OpticalPathLength);
1,353                  SetDlgItemText(MotionDatahDlg, IDD_OPL, string);
1,354          } /* end of if dialog box */
1,355
1,356          incCount /= (unsigned int)2;
1,357      } /* end of while incCount */
1,358      /* check if Ymirror has moved */
1,359      if (viewPtr->Mirror[Y] != savedCount) moved = TRUE;
1,360
1,361  } /* end of while(moved) */
1,362
1,363  /* Update the entire view plane */
1,364  ComputeViewPlane(viewPtr);
1,365
1,366  /* If OPL is less than minOPL, the rays have not hit the last */
1,367  /*    surface in the optical path. Reset mirror coords and    */
1,368  /*    try again.                                              */
1,369  if (viewPtr->Type != BOTTOM_VIEW)
1,370      if (viewPtr->OpticalPathLength < minOPL)
1,371      {
1,372          BYTE savedType;     /* temporary storage for view type */
1,373
1,374          /* Set ViewPoint to position of the last surface in the path */
```

```
1,375            opi = viewPtr->Type;
1,376            numberOfSurfaces = ModelPtr->OpticalPath[opi].NumberOfSurfaces;
1,377          - surface = numberOfSurfaces-1;
1,378            nextSurfPtr = ModelPtr->OpticalPath[opi].SurfacePtr[surface];
1,379            CopyVectD3(viewPtr->ViewPoint,nextSurfPtr->Position);
1,380
1,381            /* Compute mirror position for position of last surface */
1,382            /* FALSE = non-interactive                               */
1,383            savedType = viewPtr->Type;
1,384            viewPtr->Type = BOTTOM_VIEW;   /* prevents infinite loop */
1,385            error = ComputeMirrorFromVp(viewPtr, FALSE);
1,386            viewPtr->Type = savedType;
1,387            if (error != OK) return(ERROR2);
1,388
1,389            /* set the focus position so that the OPL is very long */
1,390            viewPtr->OpticalPathLength *= (float)3.0;
1,391            CompFocus(viewPtr);
1,392
1,393            /* go back to top of function with better seed mirror coords */
1,394            goto RETRY;
1,395         } /* end of OPL to small */
1,396
1,397      return(OK);
1,398  }
1,399  /********** end of function ComputeMirrorFromVP() ********************/
1,400
1,401  /*********************************************************************
1,402
1,403      Function Name: ComputeViewsFromObjects()
1,404
1,405      Engineer: Steve Palm
1,406
1,407      Revision History:
1,408         Created                       16:47:57 Fri 26-Apr-1991
1,409
1,410      Description: This function will compute the ViewPlane parameters and
1,411         mirror coordinates, based on the ideal position of the objects
1,412         in the view.
1,413
1,414      Call Syntax: error = ComputeViewsFromObjects()
1,415
1,416      Argument Declarations Within Function: none.
1,417
1,418      Returns: error = OK,         success
1,419                     = ERROR1,     invalid group index
1,420                     = ERROR2,     invalid object index
1,421                     = ERROR3,     invalid perspective index
1,422                     = ERROR4,     error computing view plane
1,423                     = ERROR5,     unable to open the dialog box.
1,424
1,425      Notes or Special Conditions:
1,426
1,427  *********************************************************************/
1,428  int ComputeViewsFromObjects(void)
1,429  {
```

```
1,430       double idealPoint[VECT3];         /* ideal position of view */
1,431       BYTE scan;                        /* motion scan number */
1,432       BYTE view;                        /* scan view number */
1,433       BYTE viewObject;                  /* object number in view */
1,434       BYTE numberOfScans;
1,435       BYTE numberOfViews;
1,436       BYTE numberOfViewObjects;
1,437       struct VIEW far *viewPtr;         /* pointer to view data */
1,438       BYTE gIndex;                      /* group index from view */
1,439       BYTE oIndex;                      /* object index from view */
1,440       BYTE pIndex;                      /* perspective index from view */
1,441       int error;                        /* function return code */
1,442       char string[80];                  /* character string */
1,443       int totalViews;                   /* total number of views in the motion */
1,444       int viewsComputed;                /* number of views computed so far */
1,445       int percentage;                   /* the percentage complete */
1,446       int dispPerc;                     /* percentage that is displayed in dialog box */
1,447       MSG msg;                          /* message structure */
1,448
1,449
1,450       /* launch the CompViewPlanes modeless dialog box */
1,451       CompViewPlaneshDlg = BLD_CompViewPlanesDlgFunc(MainhWnd, NULL, NULL, NULL);
1,452       if (CompViewPlaneshDlg == 0) return(ERROR5);
1,453
1,454       /* process messages that are on the que, primarally creating dlg box */
1,455       while (PeekMessage(&msg, NULL, NULL, NULL, TRUE))
1,456           if (!IsDialogMessage(CompViewPlaneshDlg, &msg))
1,457           {
1,458               TranslateMessage(&msg);
1,459               DispatchMessage(&msg);
1,460           }
1,461
1,462       /* compute the total number of views to compute */
1,463       totalViews = 0;
1,464       viewsComputed = 0;
1,465       numberOfScans = MotionPtr->NumberOfScans;
1,466       for (scan = 0; scan < numberOfScans; scan++)
1,467       {
1,468           numberOfViews = MotionPtr->ScanPtr[scan]->NumberOfViews;
1,469           totalViews += numberOfViews;
1,470       } /* end of scan loop */
1,471
1,472       /* display 0% complete */
1,473       dispPerc = 0;
1,474       wsprintf(string, "%3d", dispPerc);
1,475       SetDlgItemText(CompViewPlaneshDlg, IDD_COMPLETE, string);
1,476
1,477       /* Loop through all the scans in the Motion */
1,478       numberOfScans = MotionPtr->NumberOfScans;
1,479       for (scan = (BYTE)0; scan < numberOfScans; scan++)
1,480       {
1,481           /* Loop through all the views in each scan */
1,482           numberOfViews = MotionPtr->ScanPtr[scan]->NumberOfViews;
1,483           for (view = (BYTE)0; view < numberOfViews; view++)
1,484           {
```

```
1,485        viewPtr = MotionPtr->ScanPtr[scan]->ViewPtr[view];
1,486
1,487        numberOfViewObjects = viewPtr->NumberOfObjects;
1,488
1,489        /* if there are no View Objects go to next view */
1,490        if (numberOfViewObjects < 1)
1,491            continue;
1,492
1,493        /* Loop through each object in the view */
1,494        ZeroVectD3(idealPoint);
1,495        for (viewObject = (BYTE)0; viewObject < numberOfViewObjects; viewObject++)
1,496        {
1,497            gIndex = viewPtr->  GroupIndex[viewObject];
1,498            oIndex = viewPtr->  ObjectIndex[viewObject];
1,499            pIndex = viewPtr->PerspectIndex[viewObject];
1,500
1,501            /* Check all ViewObjects for valid indexes */
1,502            /* Check the Group Index */
1,503            if (gIndex >= PartPtr->NumberOfGroups)
1,504            {
1,505                DestroyWindow(CompViewPlaneshDlg);
1,506                sprintf(string, "*ERROR*\nInvalid Group Index %hd\n Scan%hd, View %hd, ViewObject %hd ",
1,507                    gIndex, scan, view, viewObject);
1,508                MessageBox(MainhWnd, string, "Compute Views From Objects",
1,509                    MB_OK|MB_ICONSTOP);
1,510                return(ERROR1);
1,511            } /* end of check Group Index */
1,512

1,513            /* Check the Object Index */
1,514            if (oIndex >= PartPtr->GroupPtr[gIndex]->NumberOfObjects)
1,515            {
1,516                DestroyWindow(CompViewPlaneshDlg);
1,517                sprintf(string, "*ERROR*\nInvalid Object Index %hd\nScan %hd, View %hd,
                        ViewObject %hd ",
1,518                    oIndex, scan, view, viewObject);
1,519                MessageBox(MainhWnd, string, "Compute Views From Objects",
1,520                    MB_OK|MB_ICONSTOP);
1,521                return(ERROR2);
1,522            } /* end of check Group Index */
1,523
1,524            /* Check the ViewObject Index */
1,525            if (pIndex >= PartPtr->GroupPtr[gIndex]->
1,526                ObjectPtr[oIndex]->NumberOfPerspects)
1,527            {
1,528                DestroyWindow(CompViewPlaneshDlg);
1,529                sprintf(string, "*ERROR*\nInvalid Perspective Index %hd\nScan %hd,
                        View %hd, ViewObject %hd ",
1,530                    pIndex, scan, view, viewObject);
1,531                MessageBox(MainhWnd, string, "Compute Views From Objects",
1,532                    MB_OK|MB_ICONSTOP);
1,533                return(ERROR3);
1,534            } /* end of check Group Index */
1,535
1,536            /* Accumulate data for Average Ideal Position from objects */
1,537            idealPoint[X] += (double)PartPtr->GroupPtr[gIndex]->
1,538                ObjectPtr[oIndex]->Ideal.Position[X];
```

```
1,539            idealPoint[Y] += (double)PartPtr->GroupPtr[gIndex]->
1,540                ObjectPtr[oIndex]->Ideal.Position[Y];
1,541            idealPoint[Z] += (double)PartPtr->GroupPtr[gIndex]->
1,542                ObjectPtr[oIndex]->Ideal.Position[Z];
1,543        } /* end of viewObject loop */
1,544
1,545        /* Compute the average ideal point of objects in view */
1,546        idealPoint[X] /= (double)numberOfViewObjects;
1,547        idealPoint[Y] /= (double)numberOfViewObjects;
1,548        idealPoint[Z] /= (double)numberOfViewObjects;
1,549
1,550        /* Copy the ideal point to the ViewPoint and          */
1,551        /* compute the mirror coordinates from the viewpoint. */
1,552        /* FALSE = non-interactive mode                       */
1,553        CopyVectD3(viewPtr->ViewPoint, idealPoint);
1,554        error = ComputeMirrorFromVP(viewPtr, FALSE);
1,555        if (error != OK)
1,556        {
1,557            DestroyWindow(CompViewPlaneshDlg);
1,558            sprintf(string, "ERROR = %d", error);
1,559            MessageBox(MainhWnd, string, "Error computing Mirrors and Focus",
1,560                MB_ICONEXCLAMATION);
1,561            return(ERROR4);
1,562        }
1,563
1,564        /* write percentage to the screen */
1,565        viewsComputed++;
1,566        if (totalViews != 0) /* prevent divide by zero */
1,567            percentage = (int)((float)viewsComputed/(float)totalViews*
1,568                (float)10.0 + 0.5)*(int)10;
1,569        if (percentage != dispPerc)
1,570        {
1,571            dispPerc = percentage;
1,572            wsprintf(string, "%3d", dispPerc);
1,573            SetDlgItemText(CompViewPlaneshDlg, IDD_COMPLETE, string);
1,574        } /* end of if */
1,575
1,576    } /* end of view loop */
1,577    } /* end of scan loop */
1,578
1,579    /* display 100% complete */
1,580    dispPerc = 100;
1,581    wsprintf(string, "%3d", dispPerc);
1,582    SetDlgItemText(CompViewPlaneshDlg, IDD_COMPLETE, string);
1,583
1,584    /* close the CompViewPlanes dialog box */
1,585    DestroyWindow(CompViewPlaneshDlg);
1,586
1,587
1,588    return(OK);
1,589 }
1,590 /*********** end of function ComputeViewsFromObjects() ********************/
1,591
1,592 /******************* end of module MODEL.C ********************************/
1,593
```

What is claimed is:

1. A scanning system for scanning an object located in space in up to three dimensions wherein a predetermined optical axis intersects the object, the scanning system comprising:
   a. imaging means for registering an image of the object wherein the imaging means is located along the optical axis and includes means for automatically focusing the image of the object onto the imaging means in response to a focusing signal;
   b. a first means for reflecting the object image to the imaging means, wherein the first means for reflecting the object is located along the optical axis, and wherein the first reflecting means has a first mirror axis and an angular displacement with respect to the first mirror axis and locates the object with respect to the optical axis;
   c. a second means for reflecting the object image to the imaging means, wherein the second means for reflecting the object is located along the optical axis, and wherein the second reflecting means has a second mirror axis and an angular displacement with respect to the second mirror axis and locates the object with respect to the optical axis;
   d. first servo means coupled to the first reflecting means for servoing the first reflecting means in response to a first servoing signal;
   e. second servo means coupled to the second reflecting means for servoing the second reflecting means in response to a second servoing signal;
   f. means for controlling the automatic focusing means, the first servo means, and the second servo means wherein the controlling means provides the focusing signal, the first servoing signal and the second servoing signal;
   g. reticle means located on the optical axis for registering a pattern having a plurality of positioning indicia thereon wherein each of the plurality of indicia is precisely located with respect to the other indicia on a common plane defined by the pattern of indicia wherein, the automatic focusing means focuses on the indicia and the object in a predetermined sequence, and wherein the common plane is located with respect to the optical axis.

2. The scanning system of claim 1 wherein the imaging means comprises a CCD camera.

3. The scanning system of claim 1 further comprising a plurality of optical reflecting means located above the common plane so as to provide coordinate information about the reticle means sufficient to locate the common plane in three dimensional space.

4. The scanning system of claim 1 wherein the automatic focussing means comprises a zoom lens.

5. The scanning system of claim 1 wherein a portion of the plurality of indicia form a central calibration pattern of predetermined size.

* * * * *

UNITED STATES PATENT AND TRADEMARK OFFICE
CERTIFICATE OF CORRECTION

PATENT NO. : 5,173,796

DATED : December 22, 1992

INVENTOR(S) : Steven G. Palm, et al

It is certified that error appears in the above-indentified patent and that said Letters Patent is hereby corrected as shown below:

Col. 2, line 57; "FIGS. 5a and 5b" should be -- FIGS. 5A and 5B --.
Col. 3, line 30; "zoom" should be -- zoom lens --.
Col. 3, line 42; "camera lens" should be -- lens of camera --.
Col. 4, line 14; before "is" add -- it --.
Col. 4, line 66; change "100" to -- 100B --.
Col. 4, line 67; change "102" to -- 102B --.
Col. 5, line 2; change "104" to --104B--.
Col. 5, line 5; change "106" to --106B--.
Col. 5, line 7; change "108" to --108B--.
Col. 5, line 12; change "110" to -- 110B --.
Col. 5, line 18; "mirror's" should be -- mirrors --.
Col. 5, line 22; ", an" should be -- and --.
Col. 5, line 23; "of process shown is" should be -- process is shown in --.
Col. 5, line 24; after "starts" add -- , at block 100A, --.
Col. 5, line 24; delete "a" and replace it with -- an --.
Col. 5, line 35; after "pattern" insert -- , in step --.
Col. 5, line 38; "The process then flows to block 102A where" should be --At block 102A,--.
Col. 5, line 64; change "100" to -- 100A and 100B --.
Col. 5, line 64; "FIG. 5" should be -- FIGS. 5A and 5B, respectively --.
Col. 6, Line 7; delete the word "allow" and replace it with -- allows --.
Col. 5, line 13; "102" should be -- 102A and 102B --.
Col. 6, line 14; "FIG. 5" should be -- FIGS. 5A and 5B --.
Col. 6, line 25; after "prior art", add -- (block 252) --.
Col. 6, line 28; "FIG. 5" should be -- FIGS. 5A and 5B --.
Col. 6, line 37; after the word "flows" insert -- to blocks 106A, 106B --.

UNITED STATES PATENT AND TRADEMARK OFFICE
CERTIFICATE OF CORRECTION

PATENT NO. : 5,173,796

DATED : December 22, 1992

INVENTOR(S) : Steven G. Palm. et al

It is certified that error appears in the above-indentified patent and that said Letters Patent is hereby corrected as shown below:

Col. 6, line 38; after the word "ratio", delete the number -- 106 --.
Col. 6, line 39; change "108" to -- 108A, 108B --.
Col. 6, line 50; after "dot", add -- (block 262) --.
Col. 6, line 56; "compared of" should be -- compared to --.
Col. 7, line 8; "230" should be -- 238 --.
Col. 7, lines 20 to 21; delete -- During the operation of a scanning mode. --.
Col. 7, line 31; "is" should be -- are --.
Col. 9, line 45; "comrises" should be -- comprises --.
Col. 10, line 47; after "point", add -- 362 --.

UNITED STATES PATENT AND TRADEMARK OFFICE
CERTIFICATE OF CORRECTION

PATENT NO. : 5,173,796
DATED : December 22, 1992
INVENTOR(S) : Steven G. Palm et al It is certified that error appears in the above-indentified patent and that said Letters Patent is hereby corrected as shown below:

In the Drawings

Add attached Figure 5A.

See attached correction to Figure 5 making the following changes:
    "Fig.-5" was changed to -- Fig.-5B.
    "100" was changed to -- 100B --.
    "102" was changed to -- 102B --.
    "104" was changed to -- 104B --.
    "106" was changed to -- 106B --.
    "108" was changed to -- 108B --.
    "110" was changed to -- 110B --.
    In block 100, "ITS" was changed to -- IT IS --.

Signed and Sealed this

Twenty-fifth Day of April, 1995

BRUCE LEHMAN

*Attest:*

*Attesting Officer*      *Commissioner of Patents and Trademarks*